(12) United States Patent
Imajo et al.

(10) Patent No.: US 6,300,079 B1
(45) Date of Patent: *Oct. 9, 2001

(54) POLYPEPTIDE AND PROCESS FOR MEASURING LIVING BODY COMPONENTS USING THE SAME

(75) Inventors: Nobuko Imajo; Yukari Yamagata; Hideo Katoh; Shinji Satomura; Kenji Nakamura, all of Amagasaki (JP)

(73) Assignee: Wako Pure Chemical Industries, Ltd., Osaka (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/680,855

(22) Filed: Jul. 16, 1996

(30) Foreign Application Priority Data

Jul. 18, 1995 (JP) .................................................. 7-203886
Mar. 13, 1996 (JP) .................................................. 8-084770

(51) Int. Cl.$^7$ ........................ G01N 33/538; G01N 33/573
(52) U.S. Cl. ........................... 435/7.1; 435/7.4; 436/538; 436/541; 436/824
(58) Field of Search ..................... 435/7.1, 7.4; 436/541, 436/538, 824

(56) References Cited

U.S. PATENT DOCUMENTS

| | | | |
|---|---|---|---|
| 5,352,616 | * 10/1994 | Sundrehagen | 436/501 |
| 5,459,078 | * 10/1995 | Kline et al. | 436/518 |
| 5,459,080 | * 10/1995 | Adamczyk et al. | 436/538 |
| 5,459,240 | * 10/1995 | Foxwell et al. | 530/328 |
| 5,571,729 | * 11/1996 | Nakamura et al. | 436/541 |
| 5,630,924 | * 5/1997 | Fuchs et al. | . |
| 5,662,733 | * 9/1997 | Hudson et al. | . |

FOREIGN PATENT DOCUMENTS

| | | |
|---|---|---|
| 326100 | * 8/1989 | (EP) . |
| 0357869 B1 | 3/1990 | (EP) . |
| 3-206964 | 9/1991 | (JP) . |
| 3-221865 | 9/1991 | (JP) . |
| 3-44399 | 2/1993 | (JP) . |
| 6-66800 | 3/1994 | (JP) . |
| WO 92/17194 | 10/1992 | (WO) . |

OTHER PUBLICATIONS

Harlow E, Lane D, 1988. Antibodies: A laboratory Manual, Cold Spring Harbor: Cold Spring Harbor Laboratory, 1998.*
Stryer L, 1988. Biochemistry, New York: W.H.Freeman and Company, 1988.*
Foxwell et al. Conjugation of monoclonal antibodies to a synthetic polypeptide substrate for protein kinase: A method for labeling antibodies with 32P. Br. J. Cancer 57:489–493, May 1988.*
Lin et al Construction of phosphorylatable monoclonal antibody to a tumor–associated antigen. Cancer Research 56:4250–4254, Sep. 1996.*
Morrison and Boyd, Organic Chemistry (3ird edition) pp. 597–601, 1973.*

* cited by examiner

*Primary Examiner*—Bennett Celsa
(74) *Attorney, Agent, or Firm*—Armstrong, Westerman, Hattorri, McLeland & Naughton, LLP

(57) ABSTRACT

A living body component in a sample derived from a living body can be rapidly and accurately measured by reacting the sample with a reagent comprising a combined product of an affinity substance and a polypeptide having at least three acid residues derived from a strong acid, separating the resulting complex by a method applying negative change such as using an anion-exchanger, and determining the amount of the analyte to be measured, on the basis of the amount of the complex or free combined product.

19 Claims, 6 Drawing Sheets

SEQUENCE LISTING (1) GENERAL INFORMATION:

(iii) NUMBER OF SEQUENCES: 23

(2) INFORMATION FOR SEQ ID NO:1:

```
        (i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 7
            (D) OTHER INFORMATION: /product= "B-alanine"

(xi) SEQUENCE DESCRIPTION: SEQ ID NO:1:

Ala Ser Ser Ser Ser Ser Ala
1               5

(2) INFORMATION FOR SEQ ID NO:2:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 2..4
            (D) OTHER INFORMATION: /product= "Sulfated Serine"

(ix) FEATURE:
            (A) NAME/KEY: Modified-site
            (B) LOCATION: 5
            (D) OTHER INFORMATION: /product= "B-alanine"

(xi) SEQUENCE DESCRIPTION: SEQ ID NO:2:

Ala Xaa Xaa Xaa Ala
1               5

(2) INFORMATION FOR SEQ ID NO:3:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 2..6
            (D) OTHER INFORMATION: /product= "Sulfated Serine"

(ix) FEATURE:
            (A) NAME/KEY: Modified-site
            (B) LOCATION: 7
            (D) OTHER INFORMATION: /product= "B-alanine"

(xi) SEQUENCE DESCRIPTION: SEQ ID NO:3:

Ala Xaa Xaa Xaa Xaa Xaa Ala
1               5

(2) INFORMATION FOR SEQ ID NO:4:

(i) SEQUENCE CHARACTERISTICS:
            (A) LENGTH: 10 amino acids
            (B) TYPE: amino acid
            (C) STRANDEDNESS:
            (D) TOPOLOGY: linear
```

```
    (ii) MOLECULE TYPE: peptide (ix) FEATURE:
         (A) NAME/KEY: Modified-site
         (B) LOCATION: 2..9
         (D) OTHER INFORMATION: /product= "Sulfated Serine"

(ix) FEATURE:
         (A) NAME/KEY: Modified-site
         (B) LOCATION: 10
         (D) OTHER INFORMATION: /product= "B-alanine"

(xi) SEQUENCE DESCRIPTION: SEQ ID NO:4:

Ala Xaa Xaa Xaa Xaa Xaa Xaa Xaa Xaa Ala
 1               5                  10

(2) INFORMATION FOR SEQ ID NO:5:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 1..8
         (D) OTHER INFORMATION: /product= "Sulfated Serine"

(ix) FEATURE:
         (A) NAME/KEY: Modified-site
         (B) LOCATION: 9
         (D) OTHER INFORMATION: /product= "B-alanine"

(xi) SEQUENCE DESCRIPTION: SEQ ID NO:5:

Xaa Xaa Xaa Xaa Xaa Xaa Xaa Xaa Ala
 1               5

(2) INFORMATION FOR SEQ ID NO:6:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 4..13
         (D) OTHER INFORMATION: /product= "Sulfated Serine"

(xi) SEQUENCE DESCRIPTION: SEQ ID NO:6:

Ala Ala Ala Xaa Xaa Xaa Xaa Xaa Xaa Xaa Xaa Xaa Xaa
 1               5                  10

(2) INFORMATION FOR SEQ ID NO:7:

(i) SEQUENCE CHARACTERISTICS:
        (A) LENGTH: 22 amino acids
        (B) TYPE: amino acid
        (C) STRANDEDNESS:
        (D) TOPOLOGY: linear (ii) MOLECULE TYPE: peptide (ix) FEATURE:
         (A) NAME/KEY: Modified-site
         (B) LOCATION: 2..21
         (D) OTHER INFORMATION: /product= "Sulfated Serine"
```

```
    (ix) FEATURE:
         (A) NAME/KEY: Modified-site
         (B) LOCATION: 22
         (D) OTHER INFORMATION: /product= "B-alanine"

(xi) SEQUENCE DESCRIPTION: SEQ ID NO:7:

Ala Xaa Xaa Xaa Xaa Xaa Xaa Xaa Xaa Xaa Xaa Xaa Xaa Xaa Xaa
1               5                   10                  15

Xaa Xaa Xaa Xaa Xaa Ala
            20

(2) INFORMATION FOR SEQ ID NO:8:

(i) SEQUENCE CHARACTERISTICS:
         (A) LENGTH: 13 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 2..4
         (D) OTHER INFORMATION: /product= "Sulfated Serine"

(ix) FEATURE:
         (A) NAME/KEY: Modified-site
         (B) LOCATION: 5
         (D) OTHER INFORMATION: /product= "B-alanine"

(ix) FEATURE:
         (A) NAME/KEY: Modified-site
         (B) LOCATION: 6..8
         (D) OTHER INFORMATION: /product= "Sulfated Serine"

(ix) FEATURE:
         (A) NAME/KEY: Modified-site
         (B) LOCATION: 9
         (D) OTHER INFORMATION: /product= "B-alanine"

(ix) FEATURE:
         (A) NAME/KEY: Modified-site
         (B) LOCATION: 10..12
         (D) OTHER INFORMATION: /product= "Sulfated Serine"

(ix) FEATURE:
         (A) NAME/KEY: Modified-site
         (B) LOCATION: 13
         (D) OTHER INFORMATION: /product= "B-alanine"

(xi) SEQUENCE DESCRIPTION: SEQ ID NO:8:

Ala Xaa Xaa Xaa Ala Xaa Xaa Xaa Ala Xaa Xaa Xaa Ala
1               5                   10

(2) INFORMATION FOR SEQ ID NO:9:

(i) SEQUENCE CHARACTERISTICS:
         (A) LENGTH: 10 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 2..3
         (D) OTHER INFORMATION: /product= "Sulfated Serine"

(ix) FEATURE:
         (A) NAME/KEY: Modified-site
         (B) LOCATION: 4
```

(D) OTHER INFORMATION: /product= "B-alanine"

(ix) FEATURE:
                    (A) NAME/KEY: Modified-site
                    (B) LOCATION: 5..6
                    (D) OTHER INFORMATION: /product= "Sulfated Serine"

(ix) FEATURE:
                    (A) NAME/KEY: Modified-site
                    (B) LOCATION: 7
                    (D) OTHER INFORMATION: /product= "B-alanine"

(ix) FEATURE:
                    (A) NAME/KEY: Modified-site
                    (B) LOCATION: 8..9
                    (D) OTHER INFORMATION: /product= "Sulfated Serine"

(ix) FEATURE:
                    (A) NAME/KEY: Modified-site
                    (B) LOCATION: 10
                    (D) OTHER INFORMATION: /product= "B-alanine"

(xi) SEQUENCE DESCRIPTION: SEQ ID NO:9:

Ala Xaa Xaa Ala Xaa Xaa Ala Xaa Xaa Ala
1               5                   10

(2) INFORMATION FOR SEQ ID NO:10:

(i) SEQUENCE CHARACTERISTICS:
                    (A) LENGTH: 5 amino acids
                    (B) TYPE: amino acid
                    (C) STRANDEDNESS:
                    (D) TOPOLOGY: linear (ii) MOLECULE TYPE: peptide (ix) FEATURE:
                    (A) NAME/KEY: Modified-site
                    (B) LOCATION: 2..4
                    (D) OTHER INFORMATION: /product= "Sulfated Tyrosine"

(ix) FEATURE:
                    (A) NAME/KEY: Modified-site
                    (B) LOCATION: 5
                    (D) OTHER INFORMATION: /product= "B-alanine"

(xi) SEQUENCE DESCRIPTION: SEQ ID NO:10:

Ala Xaa Xaa Xaa Ala
1               5

(2) INFORMATION FOR SEQ ID NO:11:

(i) SEQUENCE CHARACTERISTICS:
                    (A) LENGTH: 6 amino acids
                    (B) TYPE: amino acid
                    (C) STRANDEDNESS:
                    (D) TOPOLOGY: linear (ii) MOLECULE TYPE: peptide (ix) FEATURE:
                    (A) NAME/KEY: Modified-site
                    (B) LOCATION: 2..5
                    (D) OTHER INFORMATION: /product= "Sulfated Tyrosine"

(ix) FEATURE:
                    (A) NAME/KEY: Modified-site
                    (B) LOCATION: 6
                    (D) OTHER INFORMATION: /product= "B-alanine"

(xi) SEQUENCE DESCRIPTION: SEQ ID NO:11:

Ala Xaa Xaa Xaa Xaa Ala
1               5

(2) INFORMATION FOR SEQ ID NO:12:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2..5
        (D) OTHER INFORMATION: /product= "Sulfated Tyrosine"

(xi) SEQUENCE DESCRIPTION: SEQ ID NO:12:

Ala Xaa Xaa Xaa Xaa
1               5

(2) INFORMATION FOR SEQ ID NO:13:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2..6
        (D) OTHER INFORMATION: /product= "Sulfated Tyrosine"

(ix) FEATURE:
        (A) NAME/KEY: Modified-site
        (B) LOCATION: 7
        (D) OTHER INFORMATION: /product= "B-alanine"

(xi) SEQUENCE DESCRIPTION: SEQ ID NO:13:

Ala Xaa Xaa Xaa Xaa Xaa Ala
1               5

(2) INFORMATION FOR SEQ ID NO:14:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2..6
        (D) OTHER INFORMATION: /product= "Sulfated Tyrosine"

(xi) SEQUENCE DESCRIPTION: SEQ ID NO:14:

Ala Xaa Xaa Xaa Xaa Xaa
1               5

(2) INFORMATION FOR SEQ ID NO:15:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide -continued

```
    (ix) FEATURE:
         (A) NAME/KEY: Modified-site
         (B) LOCATION: 2..8
         (D) OTHER INFORMATION: /product= "Sulfated Tyrosine"

(ix) FEATURE:
         (A) NAME/KEY: Modified-site
         (B) LOCATION: 9
         (D) OTHER INFORMATION: /product= "B-alanine"

(xi) SEQUENCE DESCRIPTION: SEQ ID NO:15:

Ala Xaa Xaa Xaa Xaa Xaa Xaa Xaa Ala
1               5

(2) INFORMATION FOR SEQ ID NO:16:

(i) SEQUENCE CHARACTERISTICS:
         (A) LENGTH: 8 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 2..8
         (D) OTHER INFORMATION: /product= "Sulfated Tyrosine"

(xi) SEQUENCE DESCRIPTION: SEQ ID NO:16:

Ala Xaa Xaa Xaa Xaa Xaa Xaa Xaa
1               5

(2) INFORMATION FOR SEQ ID NO:17:

(i) SEQUENCE CHARACTERISTICS:
         (A) LENGTH: 10 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 2..9
         (D) OTHER INFORMATION: /product= "Sulfated Tyrosine"

(ix) FEATURE:
         (A) NAME/KEY: Modified-site
         (B) LOCATION: 10
         (D) OTHER INFORMATION: /product= "B-alanine"

(xi) SEQUENCE DESCRIPTION: SEQ ID NO:17:

Ala Xaa Xaa Xaa Xaa Xaa Xaa Xaa Xaa Ala
1               5                   10

(2) INFORMATION FOR SEQ ID NO:18:

(i) SEQUENCE CHARACTERISTICS:
         (A) LENGTH: 9 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 2..9
         (D) OTHER INFORMATION: /product= "Sulfated Tyrosine"

(xi) SEQUENCE DESCRIPTION: SEQ ID NO:18:
```

```
Ala Xaa Xaa Xaa Xaa Xaa Xaa Xaa Xaa
 1               5
```

(2) INFORMATION FOR SEQ ID NO:19:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2..11
        (D) OTHER INFORMATION: /product= "Sulfated Tyrosine"

(ix) FEATURE:
        (A) NAME/KEY: Modified-site
        (B) LOCATION: 12
        (D) OTHER INFORMATION: /product= "B-alanine"

(xi) SEQUENCE DESCRIPTION: SEQ ID NO:19:

```
Ala Xaa Xaa Xaa Xaa Xaa Xaa Xaa Xaa Xaa Xaa Ala
 1               5                  10
```

(2) INFORMATION FOR SEQ ID NO:20:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2..9
        (D) OTHER INFORMATION: /product= "Sulfated Serine"

(ix) FEATURE:
        (A) NAME/KEY: Modified-site
        (B) LOCATION: 10..14
        (D) OTHER INFORMATION: /product= "Sulfated Tyrosine"

(xi) SEQUENCE DESCRIPTION: SEQ ID NO:20:

```
Ala Xaa Xaa Xaa Xaa Xaa Xaa Xaa Xaa Xaa Xaa Xaa Xaa Xaa
 1               5                  10
```

(2) INFORMATION FOR SEQ ID NO:21:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1..8
        (D) OTHER INFORMATION: /product= "Sulfated Serine"

(ix) FEATURE:
        (A) NAME/KEY: Modified-site
        (B) LOCATION: 9..13
        (D) OTHER INFORMATION: /product= "Sulfated Tyrosine"

(xi) SEQUENCE DESCRIPTION: SEQ ID NO:21:

```
Xaa Xaa Xaa Xaa Xaa Xaa Xaa Xaa Xaa Xaa Xaa Xaa
1               5                   10
```

(2) INFORMATION FOR SEQ ID NO:22:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2..6
        (D) OTHER INFORMATION: /product= "Phosphated Tyrosine"

(ix) FEATURE:
        (A) NAME/KEY: Modified-site
        (B) LOCATION: 7
        (D) OTHER INFORMATION: /product= "B-alanine"

(xi) SEQUENCE DESCRIPTION: SEQ ID NO:22:

```
Ala Xaa Xaa Xaa Xaa Xaa Ala
1               5
```

(2) INFORMATION FOR SEQ ID NO:23:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 7
        (D) OTHER INFORMATION: /product= "B-alanine"

(xi) SEQUENCE DESCRIPTION: SEQ ID NO:23:

```
Ala Tyr Tyr Tyr Tyr Tyr Ala
1               5
```

POLYPEPTIDE AND PROCESS FOR MEASURING LIVING BODY COMPONENTS USING THE SAME

BACKGROUND OF THE INVENTION

This invention relates to a novel polypeptide having acid residues derived from a strong acid and a process for measurement of analytes to be measured in samples derived from living bodies, such as body fluids (e.g. serum, blood, plasma, urine, etc.), lymphocyte, hemocyte, and various cells, with the use of said polypeptide.

It is known that specific substances interact strongly on each other (namely, they have a high affinity for each other) to form a stable complex. The specific substances include, for example, the following combinations: antigen and antibody; protease and its inhibitor; sugar chain and lectin; enzyme and substrate therefor or coenzyme; physiologically active substance such as hormone, and receptor or transport protein for said active substance; and a pair of polynucleotide chains of duplex DNA.

As a method for measuring an analyte to be measured in a sample by utilizing the above interaction, the following can be exemplified: a method of forming a complex on a solid phase by the reaction of substances in the above-exemplified combination and then carrying out so-called Bound/Free (B/F) separation by use of said solid phase such as enzyme immunoassay (EIA), radioimmunoassay (RIA) and fluoroimmunoassay (FIA) (for instance, the processes disclosed in JP-A 1-22706 (EP-A-326100), JP-A 3-44399, etc.); and a method developed by some of the present inventors, e.g., a method of carrying out separation of a complex from a free analyte to be measured, i.e. the so-called B/F separation, by use of a high-pressure liquid chromatography (HPLC) (for example, the processes disclosed in JP-A 2-28557 (EP 357869), JP-A 3-206964, JP-A 3-221865, JP-A 6-66800, etc.).

In such a measuring method, the precision of measurement and the time required for analysis are influenced by the efficiency of the B/F separation to a certain extent. Therefore, various researches on the B/F separation have been conducted.

For example, in the processes disclosed in JP-A 1-227061 (EP-A 326100), JP-A 3-44399, etc., in which the B/F separation is carried out using a solid phase, and the processes disclosed in JP-A 6-66800, etc., in which the B/F separation is carried out using HPLC, the B/F separation is carried out, for example, as follows: an anionic substance is previously introduced into, for instance, an antibody to an analyte to be measured in a sample derived from a living body, and the so-called B/F separation is carried out by utilizing anionic properties of the anionic substance in a complex of the analyte and the antibody.

Such a method makes it possible to carry out the B/F separation more efficiently than before. However, in all the processes, the anionic substance used is that derived from a poly(amino acid), and the B/F separation is carried out by utilizing the anionic properties imparted by the carboxyl groups of the poly(amino acid), and thus there are found such drawbacks as mentioned below in case where the B/F separation is carried out using HPLC.

Namely, in the method using HPLC, the complex should be separated from, for example, free antibody and substances present in the sample which tend to affect the measurement, simultaneously with the B/F separation. For carrying out such separation sufficiently by utilizing the anionic properties of carboxyl groups derived from the poly(amino acid), at least about 200 carboxyl groups (about 200 amino acid residues) should be introduced into the anionic substance molecule. Accordingly, there have been the following problems. First, the preparation of the anionic substance requires much labor. Moreover, the large-scale preparation of the anionic substance with a uniform molecular weight is difficult, so that when the B/F separation is carried out by HPLC by utilizing such an anionic substance, tailing or leading of a peak occurs to lower the precision of measurement in some cases. In addition, when a poly(amino acid) having carboxyl groups, such as poly(glutamic acid) is used for the separation, a nonspecific reaction takes place to cause a phenomenon such as an increase in a blank value and measured values in some cases. For preventing the phenomenon, it is necessary to add a suitable anionic polymer such as γ-poly(glutamic acid).

Thus, there is a desire to seek further improvement.

SUMMARY OF THE INVENTION

The present invention was made in view of such conditions and is intended to provide a novel poly-peptide and a process for measuring an analyte to be measured in a sample derived from a living body which uses the polypeptide. When a complex formed by the interaction between an analyte to be measured in a sample derived from a living body and a substance having affinity for the analyte (hereinafter abbreviated as "affinity substance") is separated from free affinity substance, i.e. non-reacted affinity substance, and substances present in the sample which tend to affect the detection of the complex, by a method applying negative charge, e.g. a method using an anion-exchanger, said polypeptide can be used for separating the complex from the free affinity substance and the like more effectively.

The present invention provides a polypeptide having at least three acid residues derived from a strong acid.

The present invention also provides a combined product of the polypeptide and an affinity substance for an analyte to be measured in a sample derived from a living body.

The present invention further provides a compound, in which a maleimido group is bound through a spacer to the N-terminus of the polypeptide, and a combined product of said compound and a substance having a SH group and affinity for an analyte to be measured in a sample derived from a living body.

The present invention still further provides a reagent for measuring an analyte to be measured in a sample derived from a living body, which comprises a combined product of the polypeptide and an affinity substance for the analyte, or the combined product mentioned above having a maleimido group-spacer-polypeptide bonding.

The present invention still further provides a process for measuring a living body component which comprises reacting a sample derived from a living body with a reagent comprising a combined product of the polypeptide and an affinity substance for an analyte to be measured in the sample or a combined product of the compound having a maleimido group-spacer-polypeptide bonding and an affinity substance having a SH group and affinity for an analyte; separating the resulting complex; and determining the amount of the living body component in the sample on the basis of the amount of the complex.

DESCRIPTION OF THE PREFERRED EMBODIMENTS

Figure 1:
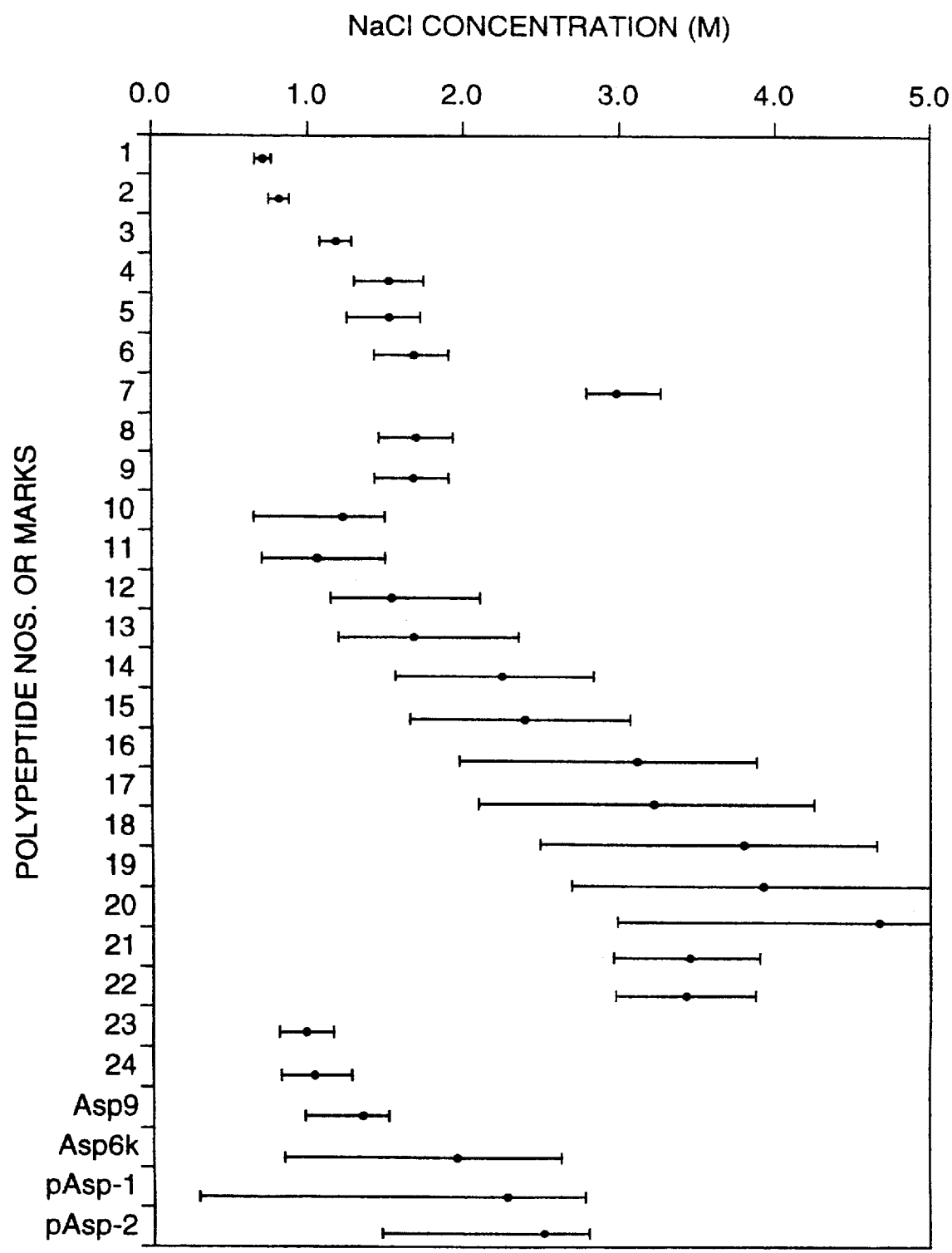
FIG. 1 shows elution positions of anionic polypeptides by a high pressure liquid chromatography (HPLC) using an anion-exchange column obtained in Example 8.

The present inventors investigated a method for separating a complex formed by the interaction between an analyte to be measured in a sample derived from a living body and an affinity substance from substances present together with the complex which tend to affect the detection of the complex, for example, free affinity substance [or free analyte; the analyte may be labeled with a substance detectable by some method (hereinafter abbreviated as "detectable substance")] by an anion-exchanger. That is, the present inventors earnestly investigated for developing a method which permits more certain separation of the complex from the free affinity substance and the like. In the course of the investigation, the present inventors found that when a substance having a suitable ability to change properties of the complex (hereinafter abbreviated as "separation-improving substance") is introduced into the complex and the complex is separated from the substances present together with the complex which tend to affect the detection of the complex, for example, the free affinity substance (or the free analyte) on the basis of the ability of the separation-improving substance, the elution position of the complex can be freely adjusted by choosing the separation-improving substance properly. In other words, the present inventors found that the introduction of a suitable separation-improving substance to the complex permits more certain separation of the complex from the free affinity substance and the like. This finding was filed for a patent (JP-A 6-66800). However, when the complex is separated by this method by introducing an anionic separation-improving substance into the complex, the above-mentioned problems are caused in some cases. In order to find an anionic separation-improving substance which does not cause such problems, the present inventors further conducted earnest investigations and consequently find that the above-mentioned problems can be solved by using, as anionic separation-improving substance, a polypeptide having at least three acid residues derived from a strong acid. Thus, the present invention has been accomplished.

The polypeptide of the present invention may be any polypeptide so long as it has at least three acid residues derived from a strong acid. The kind and number of amino acid residues constituting the poly-peptide are not particularly limited. However, when the ease of synthesis and the like are taken into consideration, the total number of the amino acid residues is properly chosen in the range of usually about 3 to about 30, preferably about 5 to about 15. As the acid residue derived from a strong acid, there can be exemplified residues derived from a strong acid having a pKa of 3 or lower such as inorganic strong acids e.g. sulfuric acid, phosphoric acid, etc.

The term "acid residue" means a retained portion of an acid after removal of a hydrogen atom, e.g. $HSO_4$.

Further, the term "amino acid residue" means a retained portion of an amino acid after removal of a hydrogen atom from the N-terminus ($-NH_2$) and a hydroxyl group from the C-terminus ($-COOH$).

The polypeptide of the present invention has any of the above-exemplified acid residues usually introduced into the reactive groups of polypeptide. As the reactive group, there can be exemplified free hydroxyl group, amino group, imino group, thiol group and the like in the polypeptide. The amino group of main chain of the polypeptide, i.e. the N-terminal amino group of the polypeptide, can also be used as the reactive group. It is preferable, however, that the acid residue is introduced into the reactive groups other than N-terminal amino group, because the free N-terminal amino group of the polypeptide can act for combining the polypeptide to an affinity substance to give a definite the mode of the combination of the polypeptide and the affinity substance to a certain extent, resulting in making the precision of measurement of an analyte in a sample derived from a living body higher.

The polypeptide of the present invention can generally be represented by the formula:

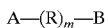

$$A-(R)_m-B \qquad [I]$$

wherein m is an integer of 3 or more; at least three R's are, the same or different, independently an amino acid residue introducing a strong acid residue thereinto via a reactive group of the amino acid residue, and the rest of R's are, the same or different, an amino acid residue having no strong acid residue, each reactive group in each side chain of the amino acid residue being able to be protected; A is a hydrogen atom, a protective group of N-terminus or an acid residue derived from a strong acid; and B is a hydroxyl group or a protective group of C-terminus.

In the above formula [I], m is an integer of at least 3, generally 3 to 30, preerably 3 to 20, more preferably 4 to 20, most preferably 5 to 15. Among a plurality of R's in the number of m, at least 3 up to m R's should be independently an amino acid residue having an acid residue derived from a strong acid. The acid residue is introduced into the amino acid residue by binding it to the reactive group of the amino acid residue. When all of R's in the number of m do not have such a strong acid residue, the rest of R's are independently an amino acid residue having no strong acid residue and in this case, the reactive group of the side chain of the amino acid residue may be protected by a conventional protecting group for N-terminus amino group. A is a hydrogen atom in the N-terminus amino group, and also this hydrogen atom may be replaced by a conventional protecting group for N-terminus amino group, and further the acid residue derived from a strong acid may also be introduced into this hydrogen atom, when it is not protected. B is a hydroxyl group at the C-terminus carboxyl group and this hydroxy group may be replaced by a conventional protecting group for C-terminus carboxyl group. In the above, the kind and sequence of m R's amino acid residues can be arbitrary.

The polypeptide of the present invention shown by the above formula [I] can be classified, for instance, into the following two groups:

(1) Polypeptide Represented by the Formula:

$$A-(R^1)_{m'}-B \qquad [II]$$

wherein $R^1$'s are, the same or different, independently an amino acid residue introducing a strong acid residue thereinto via a reactive group of the amino acid residue; m' is an integer of 3 or more; and A and B are as defined above.

In the above formula [II], m' is integer of at least 3, generally 3 to 30, preferably 3 to 20, more preferably 4 to 20, most preferably 5 to 15; $R^1$ is an amino acid residue having an acid residue derived from a strong acid. Namely, all of the amino acid residues have independently an acid residue derived from a strong acid. A and B are as defined above. In the above, the kind and sequence of $R^1$'s amino acid residues in the number of m can be arbitrary.

(2) Polypeptide Represented by the Formula:

$$A-(R^1)_{m'}-(R^2)_n-B \qquad [III]$$

wherein m' is an integer of 3 or more; at least three $R^1$'s are, the same or different, independently an amino acid residue introducing a strong acid residue thereinto via a reactive group of the amino acid residue; each $R^2$ is an amino acid residue having no strong acid residue, each reactive group in each side chain of the amino acid residue being able to be protected; n is an integer of 1 or more; and A and B are as defined above.

In the above formula [III], $R^2$ is an amino acid residue having no acid residue derived from a strong acid; (m'+n) is an integer of at least 4, generally 4 to 30, preferably 4 to 20, more preferably 5 to 20, most preferably 6 to 15; n is an integer of at least 1, generally 1 to 27, preferably 1 to 17, more preferably 1 to 16, most preferably 1 to 10; and other symbols have the same meaning as defined above. The kind and sequence of $R^1$'s amino acid residues in the number of m' and $R^2$,s amino acid residue in the number of n can be arbitrary. In this case, there are including a polypeptide composed of a block containing amino acid residues all of which have an acid residue derived from a strong acid and a block containing no such strong acid residue as mentioned just above.

The acid residues derived from a strong acid in the polypeptide are preferably acid residues derived from a polyvalent strong acid such as sulfuric acid, phosphoric acid or the like. Of these acid residues, sulfuric acid residue is preferable, particularly when the polypeptide is used as a separation improving substance, because phosphatase tends to be present in the analyte to be measured in a sample derived from a living body. It is sufficient that the strong acid residues are present in the polypeptide of the present invention in a number of at least 3. When the number of the acid residues is too large, the polypeptide is difficult to use as the separation-improving substance, for example, in the separation by an anion-exchanger, the separation and the elution from a column or the like are difficult. Therefore, when the polypeptide is used as the separation-improving substance, the number of the acid residues is properly chosen in the range of usually 3 to 30, preferably 3 to 20, more preferably 4 to 20, most preferably 5 to 15. Considering the ease of synthesis and the like, the total number of amino acid residues is properly chosen in the range of usually about 3 to about 30, preferably about 3 to about 20, more preferably about 4 to about 20, most preferably about 5 to about 15. When the number of the acid residues is less than 3, a peak of separation by the aid of the separation-improving substance and an elution peak due to a serum component overlap each other, so that the precision of measurement (analysis) is lowered. For avoiding the overlapping of the peak of separation by the aid of the separation-improving substance and the elution peak due to a component in a sample derived from a living body, such as serum to increase the precision of measurement further, the number of the acid residues is preferably 4 or more, more preferably 5 or more. In addition, when sulfuric acid residues are introduced as the acid residues derived from a strong acid, the introduction is preferably carried out by utilizing the phenolic hydroxyl groups of tyrosine residues, from the viewpoint of the stability of the sulfuric acid residues in an aqueous solution after their introduction.

In the polypeptide of the present invention, the amino acid residues having an acid residue derived from a strong acid are not particularly limited so long as they are those obtained by introducing an acid residue derived from a strong acid into each of the free reactive groups of amino acid residues, e.g. hydroxyl group, amino group, imino group, thiol group, etc. This amino acid residue includes, for example, amino acid residues having a free hydroxyl group, such as tyrosine, serine, threonine, etc.; amino acid residues having a free amino group, such as lysine, arginine, etc.; amino acid residues having a free imino group, such as histidine, tryptophan, proline, oxyproline, etc.; and amino acid residues having a free thiol group, such as cysteine, etc. When the ease of introduction of the acid residue derived from a strong acid is taken into consideration, preferable examples of the amino acid residue are serine, threonine and tyrosine. The amino acid residues in the polypeptide of the present invention are not particularly limited so long as they are those derived from conventional amino acids in the field of peptide chemistry. Preferable examples thereof are residues of amino acids such as alanine, glycine, B-alanine, etc.

The polypeptide of the present invention may be synthesized by either of the following methods, or the like: (i) a method of introducing an acid residue derived from a strong acid into each of at least three free reactive groups of a polypeptide having a proper number of free reactive groups (J. Chem. Soc. Perkin Trans I, (1990), 1739–1744, etc.), (ii) a method of synthesizing a desired polypeptide starting from as a synthesis material, amino acids having the acid residue derived from the strong acid (Chem. Pharm. Bull., 41(2), (1993), 376–380, etc.). Considering the the yield of the desired polypeptide, etc., the method (i) is preferable to the method (ii) (particularly when the number of amino acid residues is large). The above method (ii), however, has the following advantage: since sulfation is not necessary, a functional group capable of binding to an affinity substance (e.g. antibody), such as a maleimidocaproic acid residue can be introduced directly into the N-terminus of the resulting polypeptide, so that the polypeptide can be immediately combined with the affinity substance.

A method for introducing an acid residue derived from a strong acid into each of the free reactive groups of a polypeptide or the free reactive group of an amino acid is not particularly limited so long as it permits introduction of the acid residue derived from a strong acid into the free reactive group such as hydroxyl group, amino group, imino group, thiol group or the like.

More specific examples of the method are given below. A method comprising reacting a sulfating agent (e.g. $HSO_3.Cl$, $HSO_3$.dimethylformamide or $HSO_3$.pyridine) or a phosphorylating agent (e.g. a phosphoryl halide such as phosphoryl chloride or a phosphorus halide such as phosphorus trichloride) with an amino acid having a free hydroxyl group (e.g. tyrosine, serine or threonine) (or a polypeptide having residues of such an amino acid) in an amount of 1 to 20 equivalents per equivalent of the free hydroxyl group of the amino acid (or the free hydroxyl groups of the amino acid residues) at 0–40° C. for 1 to 24 hours in an anhydrous solvent [e.g. di-methylformamide (DMF) or dimethyl sulfoxide (DMSO)] by use of an alkaline substance (e.g. pyridine, triethyl-amine or NaH) as a catalyst, and thereby introducing an acid residue derived from the strong acid into the hydroxyl group of the amino acid residue (or each of the hydroxyl groups of the amino acid residues). A method comprising reacting a sulfating agent (e.g. $HSO_3.Cl$, $HSO_3$.dimethylformamide or $HSO_3$.pyridine) or a phosphorylating agent (e.g. a phosphoryl halide such as phosphoryl chloride or a phosphorus halide such as phosphorus trichloride) with an amino acid having a free amino group (e.g. lysine or arginine) (or a polypeptide having one or more residues of such an amino acid) or an amino acid having a free imino group (e.g. histidine, tryptophan, proline or oxyproline) (or a polypeptide having one or more residues of such an amino acid) in an amount of 1 to 20 equivalents per equivalent of the free amino or imino group of the amino acid (or the free amino group(s) and/or imino group(s) of the amino acid residues) at 0–40° C. for 1 to 24 hours in a solvent (anhydrous) [e.g. dimethylformamide (DMF) or dimethyl sulfoxide (DMSO)) by use of an alkaline substance (e.g. pyridine, triethylamine or NaH) as a catalyst, and thereby introducing an acid residue derived from the strong acid into the amino and/or imino group of the amino acid residue (or each of the amino group(s) and/or imino group(s) of the amino acid residues). Considering the ease of synthesis, the stability of the introduced acid residue in an aqueous solution, its stability to enzymes present in a sample derived from a living body (e.g. phosphatase), etc., sulfuric acid residue is more preferable as the acid residue derived from a strong acid which is used in the present invention.

As the polypeptide having free reactive groups such as hydroxyl groups, amino groups, imino groups, thiol groups, etc., which is used as a starting material for the polypeptide of the present invention, there can be used either a commercially available polypeptide or a polypeptide synthesized by a conventional method generally employed in the field of peptide chemistry, for example, the active ester method, mixed acid anhydride method or azide method (Nobuo Izumiya et al. "Peptide Gosei no Kiso to Jikken" (Basis and Practice of Peptide Synthesis), pp. 89–142, Jan. 20, 1985, Maruzen Co., Ltd.). For synthesizing such a polypeptide, a protecting group stable in the subsequent sulfation step is preferable as a protecting group for the N-terminal amino group. Preferable examples of the protecting group are urethane type protecting groups such as 9-fluorenylmethoxycarbonyl (Fmoc) group which are removable under alkaline conditions. Protecting groups for the reactive groups of the side chains of amino acids or amino acid residues may be properly chosen by considering, for example, the synthesis conditions of the polypeptide and the introduction conditions of the acid residues derived from a strong acid. Preferable examples of these protecting groups are t-butyl group and benzyl group.

As the affinity substance used in the present invention, any substance may be used without particular restriction so long as it has affinity for an analyte to be measured in a sample derived from a living body. Specific examples of the affinity substance are anti-bodies, antigens, and lectins (e.g. concanavalin A, Lens culinaris lectin, Phaseolus vulgaris lectin, Datura stramonium agglutinin, Triticum vulgaris lectin, etc.), which have affinity for the analyte; inhibitors for enzymes [e.g. amylase, creatine kinase (CK), glutamic-oxaloacetic transaminase (GOT)]; polynucleotide chains complementary to single-stranded polynucleotides of nucleic acids which are analytes to be measured; and receptors for thyroid-stimulating hormone, acetyl-choline, glutamic acid, etc.

As a method for preparing a combined product of the affinity substance and the polypeptide according to the present invention (hereinafter abbreviated as "the combined product of the present invention"), there can be exemplified a method of linking the specific reactive group of the affinity substance to the specific reactive group of the polypeptide; a method of replacing the specific reactive group of the affinity substance by the polypeptide; and a method of combining the affinity substance and the polypeptide through a substance having affinity for the affinity substance (e.g. antibody, lectin, antigen, inhibitor, DNA, etc.). Specifically, there can be exemplified all of the following methods and the preparation may be carried out according to any of them. 1) Conventional methods for attaching a labeling substance to an antibody which are generally employed, for example, in-conventional enzyme immunoassay (EIA), radioimmunoassay (RIA) and fluoroimmunoassay (FIA) (e.g. Yuichi Yamamura "Igaku Jikken Koza Vol. 8" 1st ed., NAKAYAMA-SHOTEN Ltd., 1971; Akira Kawano "Zusetsu Keikokotai" 1st ed., Soft Science, Inc., 1983; and Eiji Ishikawa, Tadashi Kawai and Kiyoshi Miyai "Koso Men-eki Sokuteiho" 2nd ed., IGAKU-SHOIN Ltd., 1982). 2) Conventional methods for modification and introduction of substances (e.g. Ikuzo Uritani, Kensuke Shimura, Michinori Nakamura and Masaru Funazu "Tanpakushitsu-no Kagakushushoku <Jo> <Ge>" 1st ed., GAKKAI-SHUPPAN CENTER Ltd., 1981; Yuji Inada et al. "Poly (ethylene glycol) Shushoku Tanpakushitsu" Seikagaku Vol. 62, No. 11, pp. 1351–1362, Japanese Biochemical Association, 1990; and George H. K. and Mark M. M. "DNA PROBES" STOCKTON PRESS, 1989).

Specific examples of the method of linking the specific reactive group of the affinity substance to the specific reactive group of the polypeptide are given below. There can be exemplified a method comprising reacting a compound in which a maleimide group is bound through a spacer to the N-terminus of the polypeptide of the present invention (the compound is hereinafter abbreviated as "the maleimide compound of the present invention"), with the SH group of an antibody Fab' prepared by a conventional method, and thereby preparing a combined product of the polypeptide of the present invention and the affinity substance (antibody).

The maleimide compound of the present invention, that is, a compound comprising a maleimido group bound through a spacer to the N-terminus of the polypeptide of the formula [I], can generally be represented by the formula:

$$D—E—(R)_m—B \qquad [IV]$$

wherein D is a meleimido group; E is a spacer; and R, m and B are as defined above.

The maleimide compound of the formula [IV] can be classified, for instance, into the following two groups:

(1) Maleimide Compound Represented by the Formula:

$$D—E—(R^1)_{m'}—B \qquad [V]$$

wherein D, E, $R^1$, m' and B are as defined above.

(2) Maleimide Compound Represented by the Formula:

$$D—E—(R^1)_{m'}—(R^2)_n—B \qquad [VI]$$

wherein D, E, $R^1$, $R^2$, m', n and B are as defined above.

The spacer represented by E in these formulas is not particularly limited. Any spacer may be used so long as it permits attachment of the N-terminus of the polypeptide of the present invention and a maleimide group to the ends, respectively, of the spacer, and does not hinder the introduction (or binding) of the maleimide compound of the present invention to the affinity substance such as antibody used in the present invention. Examples of the spacer are groups represented by —R⁴CO— wherein R4 is a divalent hydrocarbon group. More specific examples are groups represented by the following formulas [VII] to [IX]:

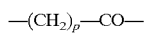  [VII]

wherein p is an integer of 1 to 10,

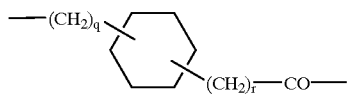  [VIII]

wherein each of q and r is zero or an integer of 1 to 5,

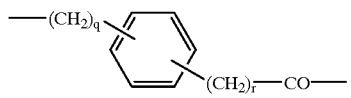  [IX]

wherein q and r are as defined above.

The alkylene groups, phenylene group and cyclohexylene group in the formulas [VII] to [IX] may have one or more substituents. The substituents include, for example, linear or branched lower alkyl groups having 1 to 4 carbon atoms, such as methyl, ethyl, propyl, butyl, etc., and hydrophilic groups such as hydroxyl, carboxyl, sulfo, amino, etc.

The maleimide compound of the present invention can easily be obtained, for example, by the following method.

The polypeptide of the present invention, a divalent crosslinking agent including a compound having a maleimido group at one end and a group reactive with amino group at the other end in an amount of 1 to 100, preferably 1 to 50, more preferably 1.2 to 10 moles per mole of the N-terminal amino group of the polypeptide, and optionally an reaction accelerator in an amount of 2 to 5 moles per mole of said amino group are reacted at 4–37° C. for 0.2 to 10 hours in a proper buffer solution having a pH of 6 to 9 or a proper organic solvent. Then, the reaction solution is purified by a suitable column chromatography, whereby the maleimide compound of the present invention can be obtained.

The divalent crosslinking agent used in the above-mentioned reaction is not particulary limited so long as it can introduce the maleimide group into the N-terminus of the polypeptide of the present invention finally. Examples thereof are crosslinking agents having a maleimide group and a succinimide group. More specific examples are succinimidyl-N-4-maleimidobutyrate, succinimidyl-N-6-maleimidocaproylate, succinimidyl-N-8-maleimidocaprylate, succinimidyl-N-11-maleimidoundecanoate, succinimidyl-N-4-(2-maleimidoethoxy)succinylate, sulfosuccinimidyl-N-4-maleimidobutyrate, sulfosuccinimidyl-N-6-maleimidocaproylate, sulfosuccinimidyl-N-8-maleimidocaprylate, succinimidyl-N-11-maleimidoundecanoate, succinimidyl-4-(N-maleimidomethyl)cyclohexane-1-carboxylate, sulfosuccinimidyl-4-(N-maleimidomethyl)cyclohexane-1-carboxylate, succinimidyl-m-maleimidobenzoate, sulfosuccinimidyl-m-maleimidobenzoate, succinimidyl-4-(p-maleimidophenyl)butyrate, sulfosuccinimidyl-4-(p-maleimidophenyl)butyrate, etc.

As the reaction accelerator, there can be exemplified bases such as triethylamine, pyridine, etc.

As the buffer solution with a pH of 6 to 9 used as a solvent for the reaction, there can be exemplified phosphate buffer, tris(hydroxymethyl)-aminomethane buffer, Good's buffers [e.g. N,N-bis(2-hydroxyethyl)glycine (Bicine) buffer, 2-[4-(2-hydroxyethyl)-1-piperazinyl]ethanesulfonic acid (HEPES) buffer, 3-morpholinopropanesulfonic acid (MOPS) buffer, etc.]. The organic solvent includes, for example, dimethylformamide (DMF) and dimethyl sulfoxide (DMSO).

The chromatography used for purifying the maleimide compound of the present invention after completion of the reaction includes, for example, gel column chromatography, silica gel column chromatography, and octadecyl silica gel (ODS) column liquid chromatography.

The organic solvent is preferable as a solvent for the reaction. This is because the decomposition of the maleimide group is slighter in the organic solvent, so that the maleimide compound of the present invention can be obtained in high yield.

The purification is preferably carried out by ODS column liquid chromatography because the-surplus divalent crosslinking agent and the maleimide compound of the present invention can be more certainly separated from each other.

The maleimide compound of the present invention obtained in the manner described above can be stably stored by treatment such as concentration to dryness, freeze-drying, etc., and hence is very useful as an intermediate for attaching the polypeptide of the present invention to the suitable affinity substance such as antibody used in the present invention.

A method for combining the maleimide compound of the present invention and the affinity substance used in the present invention to obtain the combined product of the polypeptide of the present invention and the affinity substance is, for example, as follows.

The maleimide compound of the present invention is reacted with the SH group of an antibody Fab' prepared by a conventional method, at 4–37° C. for 1 to 16 hours in a solution which does not deprive the antibody of its properties (e.g. a buffer solution usually used in the field of immunoassay), whereby the combined product of the polypeptide of the present invention and the affinity substance (antibody) can be prepared.

As a method for linking the amino group of the polypeptide of the present invention to the amino group of the affinity substance, a conventional glutaraldyhde method can be exemplified. As a method for linking the amino group of the polypeptide of the present invention to the sugar chain of the affinity substance, there can be exemplified a conventional periodic acid method which comprises treating the sugar chain with periodic acid to form an aldehyde group, and linking the aldehyde group to the amino group of the polypeptide of the present invention.

Although the polypeptide of the present invention may be introduced into the affinity substance by utilizing the reactive group in side chain of the polypeptide, it is preferably bound thereto (or introduced thereinto) by utilizing its N-teminal amino group.

The reason is as follows. Since the N-terminal amino group is usually single, the attachment to the affinity substance by use of the N-terminal amino group results in combination of the polypeptide of the present invention and the affinity substance in a molar ratio of 1:1. Therefore, when an analyte to be measured is separated using the resulting combined product, the analyte is separated as a single peak, so that the precision of a desired measurement can be further increased. The maleimide compound of the present invention is a useful substance for preparing such a combined product.

When the combined product of the present invention is prepared by utilizing the N-terminal amino group, it is preferable that no acid residue derived from a strong acid is introduced into the N-terminal amino acid residue of the polypeptide of the present invention. This is because the yield of the desired combined product is higher when the polypeptide of the present invention having no acid residue introduced into the N-terminal amino acid residue is combined with the affinity substance.

A process for measuring a living body component using the combined product of the present invention (hereinafter abbreviated as "the measuring process of the present invention") is not particulary limited so long as the process makes it possible to carry out a desired measurement by use of the combined product of the present invention. Specific examples thereof are the following processes.

(1) A process for measuring the amount of an analyte to be measured in a sample derived from a living body which utilizes a noncompetitive reaction (measuring process (1))

First, a sample derived from a living body and containing an analyte to be measured, an affinity substance labeled with a detectable substance (herein-after abbreviated as "labeled affinity substance") and the combined product of the present invention (the binding sites for the labeled affinity substance and the combined product of the present invention, respectively, in the analyte are different) are reacted by mixing, if necessary, in a suitable buffer solution, to form a complex by combination of the analyte, the labeled affinity substance and the combined product of the present invention. Then, the complex is separated from free labeled affinity substance by a method applying negative charge, for example, a machine or instrument having anion-exchange action including a HPLC apparatus equipped with a column packed with a packing material for anion-exchange chromatography, an anion-exchange membrane, or a reaction tube having an anion-exchange action. Subsequently, the amount of the detectable substance contained in the separated complex is determined by a measuring method suitable for properties of the detectable substance. Separately, measurement is carried out in the same manner as described above by using samples containing known concentrations of the analyte, and there is obtained a calibration curve showing the relationship between the amount of the analyte and the amount of the detectable substance in the complex. Using the calibration curve, the amount of the analyte corresponding to the amount of the detectable substance in the complex is determined, whereby the amount of the analyte in the sample can be measured.

In the above-mentioned reaction, the concentrations of the labeled affinity substance and the combined product of the present invention used for forming the complex are varied depending on a value at which the limit of measurement of the analyte in the sample is set. It is usually preferable that the labeled affinity substance and the combined product are present in the reaction solution in concentrations which are not less than a concentration at which they can bind to the whole analyte of a concentration corresponding to the limit of measurement, preferably 2 times or more as high as, more preferably 5 times or more as high as, most preferably 10 times or more as high as the concentration.

When the analyte itself is a substance measurable or detectable by some method, the amount of the analyte in the sample can be similarly measured by carrying out the above-mentioned reaction without the labeled affinity substance, and measuring the amount of the analyte in the resulting complex by a method suitable for properties of the analyte.

(2) A process for measuring the amount of an analyte to be measured in a sample derived from a living body which utilizes a competitive reaction (measuring process (2))

First, a sample derived from a living body and containing an analyte to be measured, analyte labeled with a detectable substance (hereinafter abbreviated as "labeled analyte") and the combined product of the present invention are reacted by mixing, if necessary, in a suitable buffer solution, to form a complex of the analyte and the combined product of the present invention, and a complex of the labeled analyte and the combined product of the present invention (hereinafter abbreviated as "labeled complex"). Then, the labeled complex is separated from free labeled analyte by a method applying negative charge, for example, a machine or instrument having anion-exchange action including a HPLC apparatus equipped with a column packed with a packing material for anion-exchange chromatography, an anion-exchange membrane, or a reaction tube having an anion-exchange action. Subsequently, the amount of the detectable substance contained in the labeled complex thus separated is determined by a measuring method suitable for properties of the detectable substance.

Separately, measurement is carried out in the same manner as described above by using samples containing known concentrations of the analyte, and there is obtained a calibration curve showing the relationship between the amount of the analyte and the amount of the detectable substance in the labeled complex. Using the calibration curve, the amount of the analyte corresponding to the amount of the detectable substance in the labeled complex is determined, whereby the amount of. the analyte in the sample can be measured.

In the above-mentioned reaction, the concentrations of the combined product of the present invention and the labeled analyte used for forming the labeled complex are not particularly limited and may be properly determined depending on values at which the limit of measurement of the analyte and the measurement sensitivity for the analyte are set, respectively. However, the concentration of the labeled analyte used should be not less than a concentration at which the labeled analyte can bind to the whole combined product of the present invention which is present in the reaction solution.

(3) A measuring process wherein analytes to be measured in a sample derived from a living body are two or more substances having the same action and the same detectable chemical characteristic (measuring process (3))

First, a sample derived from a living body and containing analytes to be measured is reacted with a substance which binds specifically to at least one of the analytes but does not bind to at least one of the other analytes and which has the polypeptide of the present invention bound thereto (or introduced thereinto) (the substance is hereinafter abbreviated as "combined product A of the present invention") by mixing, if necessary, in a suitable buffer solution.

Thus, there is formed a complex of specific analyte(s) in the sample and the combined product A of the present invention. Then, the complex is separated from free analyte(s) by a method applying negative charge, for example, a machine or instrument having anion-exchange action including a HPLC apparatus equipped with a column packed with a packing material for anion-exchange chromatography, an anion-exchange membrane, or a reaction tube having an anion-exchange action. Subsequently, the amount of the analyte(s) contained in the separated complex or the amount of free analyte(s), or both, are determined by a measuring method suitable for properties of the analytes. Separately, measurement is carried out in the same manner as described above, for example, by using samples containing known concentrations of the analyte, and there is obtained a calibration curve showing the relationship between the amount of the analyte and the measured value actually obtained property of the analyte in the complex. Using the calibration curve, the amount of the analyte corresponding to the measured value is determined, whereby the amount of any of the analytes in the sample can be measured.

In the above-mentioned reaction, the concentration of the combined product A of the present invention used for forming the complex is not particularly limited and may be properly determined depending on values at which the limit of measurement of the analyte and the measurement sensitivity for the analyte are set, respectively.

(4) A measuring process wherein analytes to be measured in a sample derived from a living body are two or more substances having the same action or having different actions in spite of their similar structures (measuring process (4))

First, a sample derived from a living body and containing analytes to be measured is reacted with a substance having affinity for all the analytes (hereinafter abbreviated as "affinity substance A") which has been labeled with a detectable substance (hereinafter abbreviated as "labeled affinity substance A") and a substance which has affinity for at least one specific analyte among the analytes and has the polypeptide of the present invention introduced thereinto (the substance is hereinafter abbreviated as "combined product B of the present invention") by mixing, if necessary, in a suitable buffer solution. Thus, there are formed a complex of analyte(s) and the labeled affinity substance A (hereinafter abbreviated as "complex A"), and a complex of the specific analyte(s), the labeled affinity substance A and the combined product B of the present invention (hereinafter abbreviated as "complex B"). Then, the complex A, the complex B and free labeled affinity substance A are separated from one another by a method applying negative change, for example, a machine or instrument having anion-exchange action including a HPLC apparatus equipped with a column packed with a packing material for anion-exchange chromatography, an anion-exchange membrane, or a reaction tube having an anion-exchange action. Subsequently, the amount of the detectable substance contained in the separated complex A or the amount of the detectable substance contained in the separated complex B, or both, are determined by a measuring method suitable for properties of the detectable substance. Separately, measurement is carried out in the same manner as described above, for example, by using samples containing known concentrations of the analyte, and there is obtained a calibration curve showing the relationship between the amount of the analyte and the amount of the detectable substance contained in the complex A and/or the amount of the detectable substance contained in the complex B. Using the calibration curve, the amount of the analyte corresponding to the amount of the detectable substance in the complex(es) is determined, whereby the amount of any of the analytes in the sample can be measured. When the affinity substance A itself is a measurable or detectable by some method, the amount of the analyte in the sample can be similarly measured by carrying out the above-mentioned reaction by use of the affinity substance A not labeled with the detectable substance, and measuring the amount of the affinity substance A in the resulting complex by a method suitable for properties of the affinity substance A.

(5) A measuring process wherein analytes to be measured in a sample derived from a living body are two substances having the same action or having different actions in spite of their similar structures (measuring process (5))

First, a sample derived from a living body and containing analytes to be measured is reacted with a labeled affinity substance A, a substance which has affinity for analyte 1 in the sample and has a polypeptide 1 of the present invention introduced thereinto (the substance is hereinafter abbreviated as "combined product C of the present invention") and a substance which has affinity for analyte 2 in the sample and has a polypeptide 2 of the present invention introduced thereinto (the substance is hereinafter abbreviated as "combined product D of the present invention") by mixing, if necessary, in a suitable buffer solution. Thus, there are formed a complex of the analyte 1, the combined product C of the present invention and the labeled affinity substance A (hereinafter abbreviated as "complex C") and a complex of the analyte 2, the combined product D of the present invention and the labeled affinity substance A (hereinafter abbreviated as "complex D"). Then, the complex C, the complex D and free labeled affinity substance A are separated from one another on the basis of the difference in properties between the polypeptides 1 and 2 by a method applying negative charge, for example, a machine or instrument having anion-exchange action including a HPLC apparatus equipped with a column packed with a packing material for anion-exchange chromatography, an anion-exchange membrane, or a reaction tube having an anion-exchange action. Subsequently, the amount of the detectable substance-contained in the separated complex C or the amount of the detectable substance contained in the separated complex D, or both, are determined by a measuring method suitable for properties of the detectable substance. Separately, measurement is carried out in the same manner as described above, for example, by using samples containing known concentrations of the analyte, and there is obtained a calibration curve showing the relationship between the amount of the analyte 1 (or 2) and the amount of the detectable substance contained in the complex C and/or the amount of the detectable substance contained in the complex D. Using the calibration curve, the amount of the analyte corresponding to the amount of the detectable substance in the complex(es) is determined, whereby the amount of either of the analytes in the sample can be measured.

When the affinity substance A itself is a measurable or detectable by some method, the amount of the analyte in the sample can be similarly measured by carrying out the above-mentioned reaction by use of the affinity substance A not labeled with the detectable substance, and measuring the amount of the affinity substance A in the resulting complex by a method suitable for properties of the affinity substance A.

(6) A measuring method wherein analytes to be measured in a sample derived from a living body are two or more forms of glycoproteins which are different in sugar chain structure but have substantially the same protein structure (measuring process (6))

First, a sample derived from a living body and containing two or more forms of glycoproteins to be measured is reacted with a lectin capable of recognizing the sugar chain structure of at least one of these glycoprotein analytes to be measured, and a combined product of the polypeptide of the present invention and an antibody which has a property of binding to all the glycoprotein analytes but is kept from binding to glycoprotein analytes(s) having the lectin introduced thereinto (the combined product is hereinafter abbreviated as "polypeptide-combined antibody"), and an antibody which can bind to all the glycoprotein analytes including the glycoprotein analyte(s) having the lectin introduced thereinto, and has a detectable substance introduced thereinto (this antibody is hereinafter abbreviated as "labeled anti-glycoprotein antibody"). Thus there are formed a complex of glycoprotein(s), the lectin and the labeled anti-glycoprotein antibody, and a complex of glycoprotein(s), the polypeptide-combined antibody and the labeled anti-glycoprotein antibody. Then, these complexes are separated from free labeled anti-glycoprotein antibody by a method applying negative charge, for example, a machine or instrument having anion-exchange action including a HPLC apparatus equipped with a column packed with a packing material for anion-exchange chromatography, an anion-exchange membrane, or a reaction tube having an anion-exchange action. Subsequently, the amount of the detectable substance contained in each or either of the separated complexes is determined by a measuring method suitable for properties of the detectable substance. Separately, measurement is carried out in the same manner as described above, for example, by using samples containing known concentrations of the glycoprotein analyte, and there is obtained a calibration curve showing the relationship between the amount of the glycoprotein analyte and the amount of the detectable substance contained in each or either of the complexes. Using the calibration curve, the amount of the glycoprotein analyte corresponding to the amount of the detectable substance in the complex(es) is determined, whereby the amount of any of the glycoprotein analytes in the sample can be measured.

When the glycoprotein analyte itself is measurable (detectable) by some method, the above-mentioned measurement can, of course, be carried out without the labeled anti-glycoprotein antibody.

An analyte in a sample derived from a living body which can be measured by any of the measuring processes (1) and (2) developed by applying the present invention is not particularly limited so long as it satisfies the following condition i) or ii). i) There exists a substance which can form a stable complex with the analyte by a high affinity between the substance and the analyte, and said substance can be measured (detected) in itself by some method or can be labeled with some detectable substance. ii) The analyte itself can be labeled with some detectable substance, and there exists a substance which can form a stable labeled complex with the analyte by a high affinity between the substance and the analyte. Typical examples of the analyte are proteins, peptides, nucleic acids, sugar chains, lipids, hormones, drugs, etc. which are contained in samples derived from living bodies, for example, body fluids such as serum, blood, plasma, urine and the like, lymphocytes, hemocytes, and various cells. More specific examples of the analyte are tumor markers such as α-fetoprotein (AFP), CA19-9, prostate specific antigen (PSA), carcinoembryonic antigen (CEA), substances having special sugar chains which is produced by cancerous cells, and the like; serum proteins such as immunoglobulin A (IgA), immunoglobulin E (IgE), immunoglobulin G (IgG), $B_2$-microglobulin, albumin, ferritin, and the like; peptides such as C-peptide, angiotensin I, and the like; enzymes such as amylase, alkaline phosphatase, γ-glutamyltransferase (γ-GTP), and the like; antiviral antibodies against clinically noted viruses such as rubella virus, herpesvirus, hepatitis virus, ATL virus, AIDS virus, and the like; deoxyribonucleic acid (DNA) and ribonucleic acid (RNA) of pathogens such as viruses and the like, or single-stranded polynucleotides constituting nucleic acids described above; antigenic substances derived from pathogens such as virus and the like; antibodies reactive with allergens such as pollen of trees and plants (e.g. cryptomeria), indoor dust and the like; lipids such as lipoproteins and the like; proteases such as trypsin, plasmin, serin protease, and the like; hormones such as insulin, human chorionic gonadotropin (hCG), thyroxine (T4), triiodothyronine (T3), prolactin, thyroid stimulating hormone (TSH), and the like; drugs such as digoxin, phenytoin, morphine, nicotine, and the like; and receptors for thyroid stimulating hormone, acetylcholine, glutamic acid, etc.

The affinity substance for an analyte to be measured in a sample derived from a living body which is used for preparing the labeled affinity substance in the measuring process (1) developed by applying the present invention is not particularly limited so long as it forms a stable complex with the analyte by a high affinity between the affinity substance and the analyte, and if necessary, the affinity substance can be measured or detected in itself by some method or can be labeled with some measurable or detectable substance. The affinity substance includes, for example, antibodies against substances having antigenicity including haptens; antigens against antibodies; lectins having affinity for sugar chains having a specific structure, such as concanavalin A, Lens culinaris lectin, Phaseolus vulgaris lectin, Datura stramonium agglutinin, Triticum vulgaris lectin, and the like; inhibitors for specific enzymes, such as al-anti-trypsin for trypsin, $\alpha_2$-macroglobulin for plasmin, $\alpha_2$-macroglobulin and $\alpha_1$-anti-chymotrypsin for serine protease, and the like; polynucleotide chains complementary to single-stranded polynucleotides which are analytes to be measured in samples derived from living bodies; and receptors for hormones.

The affinity substance for an analyte to be measured in a sample derived from a living body which is used for preparing the combined product of the present invention in the measuring processes (1) and (2) developed by applying the present invention is not particularly limited so long as it forms a stable complex with the analyte or labeled analyte, or a complex of the analyte and labeled affinity substance by a high affinity between the affinity substance and the analyte or the labeled analyte or the complex. The affinity substance includes, for example, antibodies against substances having antigenicity including haptens; antigens against antibodies; lectins having affinity for sugar chains having a specific structure, such as concanavalin A, Lens culinaris lectin, Phaseolus vulgaris lectin, Datura stramonium agglutinin, Triticum vulgaris lectin, and the like; inhibitors for specific enzymes, such as $\alpha_1$-anti-trypsin for trypsin, $\alpha_2$-macroglobulin for plasmin, $\alpha_2$-macroglobulin for serine protease, and the like; and polynucleotide chains complementary to single-stranded polynucleotides which are analytes to be measured in samples derived from living bodies (the binding site for these substances is different from that for the affinity substance used for preparing the labeled affinity substance).

Analytes in a sample derived from a living body which can be measured by the measuring process (3) developed by applying the present invention are not particularly limited so long as they are per se measurable or detectable by some method and there exists a substance which can form a stable complex with at least one of the analytes by a high affinity between the substance and the analyte(s) but does not bind to at least one of the other analytes. Typical examples of the analytes are enzymes and the like which are contained in samples derived from living bodies, for example, body fluids such as serum, blood, plasma, urine and the like, lymphocytes, hemocytes, and various cells. More specific examples of the analytes are enzymes such as amylase, alkaline phosphatase, acid phosphatase, γ-glutamyltransferase (γ-GTP), lipase, creatin kinase (CK), lactate dehydrogenase (LDH), glutamic-oxaloacetic transaminase (GOT), glutamic-pyruvic transaminase (GPT), renin, protein kinase (PK), tyrosine kinase, etc.

The affinity substance for specific analyte(s) to be measured in a sample derived from a living body which is used for preparing the combined product A of the present invention in the measuring process (3) developed by applying the present invention is not particularly limited so long as it can form a stable complex with at least one of analytes to be measured in the sample by a high affinity between the affinity substance and the analyte(s) but does not bind to at least one of the other analytes. The affinity substance includes, for example, antibodies against specific partial structures or antigenic determinants of substances having antigenicity (including haptens); lectins having affinity for sugar chains having a specific structure, such as concanavalin A, Lens culinaris lectin, Phaseolus vulgaris lectin, Datura stramonium agglutinin, Aleuria aurantia lectin, Ricinus communis lectin, Arachis hypogaea lectin, Triticum vulgaris lectin, etc.; and inhibitors for enzymes such as amylase, creatin kinase (CK), glutamic-oxaloacetic transaminase (GOT), etc.

Analytes in a sample derived from a living body which can be measured by the measuring process (4) developed by applying the present invention are not particularly limited so long as they satisfy the following conditions i) and ii). i) There exists a substance which binds to all the analytes in the sample and which has in itself a property detectable by some method or can be labeled with a detectable substance. ii) There exists a substance which can form a stable complex with at least one of the analytes by a high affinity between the substance and the analyte(s) but does not bind to at least one of the other analytes. Typical examples of the analytes are enzymes, physiologically active substances, tumor associated antigens, substances having a sugar chain, etc. which are contained in samples derived from living bodies, for example, body fluids such as serum, blood, plasma, urine and the like, lymphocytes, hemocytes, and various cells. More specific examples of the analytes are preferably enzymes such as amylase, alkaline phosphatase, acid phosphatase, γ-glutamyltransferase (γ-GTP), lipase, creatin kinase (CK), lactate dehydrogenase (LDH), glutamic-oxaloacetic transaminase (GOT), glutamic-pyruvic transaminase (GPT), renin, protein kinases, tyrosine kinase, etc.; physiologically active substances such as steroid hormones, human chorionic gonadotropin (hCG), prolactin, thyroid stimulating hormone (TSH), luteinizing hormone (LH), etc.; and tumor associated antigen such as prostate specific antigen (PSA), α$_2$-macroglobulin, carcinoembryonic antigen (CEA), α-fetoprotein, etc.

The affinity substance for analytes to be measured in a sample derived from a living body which is used for preparing the labeled affinity substance A in the measuring process (4) developed by applying the present invention is not particularly limited so long as it can bind to all the analytes in the sample and it has in itself a property detectable by some method or can be labeled with a detectable substance. Specific examples of the affinity substance are antibodies against specific partial structures or antigenic determinants of substances having antigenicity including haptens; lectins having affinity for sugar chains having a specific structure, such as concanavalin A, Lens culinaris lectin, Phaseolus vulgaris lectin, Datura stramonium agglutinin, Aleuria aurantia lectin, Ricinus communis lectin, Arachis hypogaea lectin, Triticum vulgaris lectin, etc.; and inhibitors for enzymes such as amylase, creatin kinase (CK), glutamic-oxaloacetic transaminase (GOT), etc.

The substance having affinity for specific analyte(s) to be measured in a sample derived from a living body which is used for preparing the combined product B of the present invention in the measuring process (4) developed by applying the present invention is not particularly limited so long as it satisfies the following conditions i) and ii), or iii). i) It does not inhibit a reaction for forming a complex of analyte(s) and free labeled affinity substance A and a reaction for detecting a detectable substance (or affinity substance A) in the complex. ii) It has affinity for specific analyte(s) in the sample. iii) When labeled affinity substance A has a detectable substance introduced thereinto, the affinity substance for specific analyte(s) in the sample has affinity for this detectable substance. Preferable specific examples of the affinity substance for specific analyte(s) in the sample are antibodies and lectins (e.g. concanavalin A, Lens culinaris lectin, Phaseolus vulgaris lectin, Datura stramonium agglutinin, Triticum vulgaris lectin, etc.) (the binding site for these substances is different from that for affinity substance A), which have affinity for the specific analyte(s); and antibodies and lectins (e.g. concanavalin A, Lens culinaris lectin, Phaseolus vulgaris lectin, Datura stramonium agglutinin, Triticum vulgaris lectin, etc.), which have affinity for affinity substance A or the detectable substance.

Analytes in a sample derived from a living body which can be measured by the measuring process (5) developed by applying the present invention are not particularly limited so long as they satisfy the following conditions i) and ii), or iii). i) There exists a substance which binds to all the analytes in the sample and which has in itself a property detectable by some method or can be labeled with a detectable substance. ii) There exists a substance which can form a stable complex with an analyte 1 in the sample by a high affinity between the substance and the analyte 1 but does not bind to an analyte 2 in the sample. iii) There exists a substance which form a stable complex with the analyte 2 by a high affinity between the substance and the analyte 2 but does not bind to the analyte 1. Typical examples of the analytes are enzymes, physiologically active substances, tumor associated antigens, substances having a sugar chain, etc. which are contained in samples derived from living bodies, for example, body fluids such as serum, blood, plasma, urine and the like, lymphocytes, hemocytes, and various cells. More specific examples of the analytes are preferably enzymes such as amylase, alkaline phosphatase, acid phosphatase, γ-glutamyltransferase (γ-GTP), lipase, creatin kinase (CK), lactate dehydrogenase (LDH), glutamic-oxaloacetic transaminase (GOT), glutamic-pyruvic transaminase (GPT), renin, protein kinases, tyrosine kinase, etc.; physiologically active substances such as steroid hormones, human chorionic gonadotropin (hCG), prolactin, thyroid stimulating hormone (TSH), luteinizing hormone (LH), etc.; and tumor associated antigen such as prostate gland specific antigen (PSA), α$_2$-macroglobulin, carcinoembryonic antigen (CEA), α-fetoprotein, etc.

The affinity substance for analytes to be measured in a sample derived from a living body which is used for preparing the labeled affinity substance A in the measuring process (5) developed by applying the present invention is not particularly limited so long as it can bind to all the analytes in the sample and it has in itself a property detectable by some method or can be labeled with a detectable substance. Specific examples of the affinity substance are antibodies against specific partial structures or antigenic determinants of substances having antigenicity (including haptens); lectins having affinity for sugar chains having a specific structure, such as concanavalin A, Lens culinaris lectin, Phaseolus vulgaris lectin, Datura stramonium agglutinin, Aleuria aurantia lectin, Ricinus communis lectin, Arachis hypogaea lectin, Triticum vulgaris lectin, etc.; and inhibitors for enzymes such as amylase, creatin kinase (CK), glutamic-oxaloacetic transaminase (GOT), etc.

The substance having affinity for the specific analyte 1 or 2 to be measured in a sample derived from a living body which is used for preparing the combined product C or D, respectively, of the present invention in the measuring process (5) developed by applying the present invention is not particularly limited so long as it satisfies the following conditions i) and ii). i) It does not inhibit a reaction for forming a complex of the analyte 1 or 2 and free labeled affinity substance A and a reaction for detecting a detectable substance (or affinity substance A) in the complex. ii) It has affinity for the specific analyte 1 or 2. Preferable specific examples of the affinity substance for the specific analyte 1 or 2 are as follows: antibodies and lectins (e.g. concanavalin A, Lens culinaris lectin, Phaseolus vulgaris lectin, Datura stramonium agglutinin, Triticum vulgaris lectin, etc.) (the binding site for these substances is different from that for affinity substance A), which have affinity for the specific analyte 1 or 2; and antibodies and lectins (e.g. concanavalin A, Lens culinaris lectin, Phaseolus vulgaris lectin, Datura stramonium agglutinin, Triticum vulgaris lectin, etc.), which have affinity for affinity substance A or the detectable substance.

The lectin used in the measuring process (6) developed by applying the present invention is not particularly limited, and a lectin having an ability to recognize an objective sugar chain structure may be properly selected from various lectins such as concanavalin A, Lens culinaris lectin, Phaseolus vulgaris lectin, Datura stramonium agglutinin, Triticum vulgaris lectin, etc.

As the antibodies used for preparing the polypeptide-combined antibody and the labeled anti-glycoprotein antibody, respectively, in the measuring process (6) developed by applying the present invention, either of the following polyclonal antibodies and monoclonal antibodies may be used so long as they have the properties described above: e.g. polyclonal antibodies prepared by immunizing animals such as horse, cattle, sheep, rabbit, goat, rat, mouse, etc. with an analyte(s) to be measured, according to a conventional method, for example, the method described in Tadashi Matsuhashi et al. "Men-ekigaku Jikken Nyumon" 2nd ed., GAKKAI-SHUPPAN CENTER Ltd., 1981, etc., and monoclonal antibodies produced by Hybridomas obtained by fusing cells from a tumor line of mouse together with mouse spleen cells previously immunized with an analyte(s) to be measured, according to the conventional method, i.e., the cell fusion method established by G. Kohler and C. Milstein (Nature, 256, 495, 1975). These polyclonal and/or monoclonal antibodies may be used singly or in proper combination of two or more thereof.

As the glycoprotein which can be separated and measured by the measuring process (6) developed by applying the present invention, any glycoptotein can be exemplified without particular restriction so long as it satisfies the following conditions: it is contained in a sample derived from a living body, for example, a body fluid (e.g. serum, blood, plasma or urine), lymphocyte, hemocyte, or any of various cells, it can have forms which are different in sugar chain structure but have substantially the same protein structure, and there exist a lectin capable of recognizing the specific sugar chain structure of at least one of the forms of glycoprotein to be measured and an antibody from which the polypeptide-combined antibody can be prepared. Preferable examples of the glycoprotein are enzymes such as amylase, alkaline phosphatase, acid phosphatase, γ-glutamyltransferase (γ-GTP), lipase, creatin kinase (CK), lactate dehydrogenase (LDH), glutamic-oxaloacetic transaminase (GOT), glutamic-pyruvic transaminase (GPT), renin, protein kinases, tyrosine kinase, etc.; physiologically active substances such as human chorionic gonadotropin (hCG), thyroid stimulating hormone (TSH), luteinizing hormone (LE), etc.; tumor associated antigen such as prostate specific antigen (PSA), $\alpha_2$-macroglobulin, carcinoembryonic antigen (CEA), α-fetoprotein, etc.; and glycogenic cancer antigens such as CA 19-9, CA 125, etc.

The concentrations of the reagents used in the measuring process (6) according to the present invention are explained below.

First, the concentration of the lectin used is varied depending on the kind of the lectin used, properties of the glycoprotein analytes to be measured, etc. It is preferable that the lectin is present together with the glycoprotein analytes in a concentration of usually 10 times or more, preferably 100 times or more, more preferably 1,000 times or more, as high as a set detection limit concentration of the glycoprotein analytes.

The concentration of the polypeptide-combined antibody, i.e. a combined product of the present invention, used is varied depending on a value at which the detection limit of the glycoprotein analytes to be measured is set. The concentration is preferably determined in view of the difference between the lectin and the polypeptide-combined antibody in association constant for the glycoprotein analytes. Although the concentration is varied depending on, for example, the kinds and properties of the glycoprotein analytes and the lectin and properties of the polypeptide-combined antibody, the concentration is preferably determined by utilizing, for example, the following general formula:

Concentration of the polypeptide-combined antibody≦(association constant of the lectin)÷(association constant of the polypeptide-combined antibody)×(concentration of the lectin)

The association constant in the above general formula refers to a association constant obtained in the equilibrium reaction represented by the formula (1) described below and is calculated by the equation (2) described below:

$$[A]+[B] \leftrightarrow [A \cdot B] \tag{1}$$

$$\text{Association constant} = [A \cdot B]/([A] \times [B]) \tag{2}$$

wherein [A]: the concentration (M) of the lectin or the polypeptide-combined antibody in an equilibrium state,
[B]: the concentration (M) of free glycoprotein analyte(s) to be measured in an equilibrium state, -continued

| | |
|---|---|
| [A · B]: | the concentration (M) of a complex of the lectin (or the polypeptide-combined antibody) and glycoprotein analyte(s). |

More specifically, for example, when the association constant of the lectin for the glycoprotein analytes is $1\times10^6$ $M^{-1}$ and the association constant of the polypeptide-combined antibody for the glycoprotein analytes is $1\times10^8$ $M^{-1}$, the concentration of the polypeptide-combined antibody is one-hundredth or less, preferably one-thousandth or less, as high as the lectin concentration. Although the concentration of the polypeptide-combined antibody used is preferably not less than a concentration at which the polypeptide-combined antibody can bind to the whole of the glycoprotein analytes to be measured of a concentration corresponding to a set detection limit, it may be lower than (for example, about one-tenth) the above-mentioned concentration.

The concentration of the labeled anti-glycoprotein antibody used is varied depending on a concentration at which the detection limit of the glycoprotein analytes is set. It is preferable to adjust the concentration of the labeled anti-glycoprotein antibody in the reaction solution to a concentration which is not less than a concentration at which the labeled anti-glycoprotein antibody can bind to the whole of the glycoprotein analytes of a concentration corresponding to the detection limit, preferably twice or more as high as, more preferably 5 times or more as high as, most preferably 10 times or more as high as the concentration.

In practicing any of the measuring processes (1) to (6) developed by applying the present invention, any of the following methods applying negative charge may be employed in place of the above-mentioned HPLC, for separating the complex(s) from free affinity substance including free labeled affinity substance, analyte(s) to be measured including labeled analyte(s), etc.: methods for electrical separation of substances on the basis of their difference in electrical charge which are usually employed in the art, for example, electro-kinetic separation using no carrier for separation (JP-B 7-111398, etc.), electrophoresis using a carrier for separation, capillary electrophoresis, a method comprising accelerating a nucleic acid hybridization, antigen-antibody reaction or the like by utilizing the electrical charge difference, and then separating free polynucleotide chain, free antibody or the like (International Publication No. WO 95/12808, etc.). In the electrophoresis using a carrier for separation among these methods, any carrier may be used without particular restriction so long as it is a carrier usually used in the art, for example, filter paper, gel (e.g. agar gel, agarose gel, polyarylamide gel or starch gel), or cellulose acetate membrane.

The detectable substance to be used for labeling the affinity substance or the analyte in the measuring processes according to the present invention includes, for example, enzymes such as alkaline phosphatases, β-galactosidase, peroxidase, micro-peroxidase, glucose oxidase, glucose-6-phosphate de-hydrogenase, acetylcholinesterase, malate dehydrogenase, luciferase, etc., which are used, for example, in enzyme immunoassay (EIA); radioisotopes such as $^{99m}Tc$, $^{131}I$, $^{125}I$, $^{14}C$, $^3H$, etc., which are used, for example, in radioimmunoassay (RIA); substances which can emit fluorescence, such as fluorescein, dansyl residue, fluorescamine, coumarin, naphthylamine, derivatives thereof, etc., which are used, for example, in fluoroimmunoassay (FIA); luminescent substances such as luciferin, isoluminol, luminol, bis(2,4,6-trifluorophenyl) oxalate, etc.; substances which can absorb an ultraviolet light, such as phenol, naphthol, anthracene, derivatives thereof, etc.; and substances having properties as spin labels, which are represented by compounds having an oxyl group, such as 4-amino- 2,2,6,6-tetramethylpiperidin-1-oxyl, 3-amino-2,2, 5,5-tetramethylpyrrolidin-1-oxyl, 2,6-di-t-butyl-α-(3,5-di-t-butyl-4-oxo-2,5-cyclohexadien-1-ylidene)-p-tolyloxy, etc. Needless to say, the detectable substance is not limited to these substances.

As a method for labeling the affinity substance with the above-exemplified detectable substance, there can be exemplified all of conventional labeling methods which are generally employed, for example, in conventional EIA, RIA and FIA (e.g. Yuichi Yamamura "Ikagaku Jikken Koza Vol. 8" 1st ed., NAKAYAMA-SHOTEN Ltd., 1971, Akira Kawano "Zusetsu Keikokotai" 1st ed., Soft Science, Inc., 1983; and Eiji Ishikawa, Tadashi Kawai and Kiyoshi Miyai "Koso Men-eki Sokuteiho" 2nd. ed., IGAKU-SHOIN Ltd., 1982). The labeling may be carried out according to these method. Needless to say, a conventional method utilizing the reaction of avidin (or streptoavidin) with biotin may be employed as a labeling method.

As the affinity substance per se measurable or detectable by some method which is used in the present invention, there can be exemplified the following substances which themselves have the above-mentioned property as the detectable substance: for example, enzymes, substances which can emit fluorescence, luminescent substances, substances which can absorb an ultraviolet light, etc.

In the measuring process of the present invention, the elution time of the complex can be freely controlled by choosing the kind of the polypeptide of the present invention (the kind and number of introduced acid residues derived from a strong acid, the kind of constituent amino acid residues, etc.). Therefore, by taking advantage of this characteristic of the process, separating and measuring analytes to be measured can be achieved.

That is, simultaneous measurement (separation and measurement) of a plurality of analytes to be measured becomes possible when there are used two or more polypeptides of the present invention which are different in the number of acid residues derived from a strong acid, and there are properly chosen the kinds of affinity substances into which the polypeptides are introduced, respectively.

Even if a sample contains a plurality of serum components which influence the measurement, making the ionicity of the complex larger than that of the serum components by use of the polypeptide of the present invention is effective in avoiding an influence on the measurement exerted by the serum components. In this case, the time required for the analysis can be reduced by utilizing a stepwise gradient.

In addition, since a material for chromatography (e.g. gel material, membrane material, glass material, etc.) used in an anion-exchange method generally has a high exchange capacity (absolute adsorption capacity for ionic substance), the whole of the complex, to which the combined product of the present invention is bound, can be adsorbed on the carrier even in the analysis of a sample containing a large absolute amount of ionic substances together with analytes to be measured, such as a sample derived from a living body, for example, serum. Therefore, said complex can be eluted at a position at which the influence of the substances present together with the analytes can be substantially avoided. Furthermore, since the polypeptide used in the measuring process of the present invention has a high water-solubility, the water-solubility of the complex to which the polypeptide is bound is higher than before the binding. Therefore, in the measuring process of the present invention, denaturation and deactivation of the analytes to be measured hardly occur during the formation of the complex having the separation-improving substance (the polypeptide) introduced thereinto.

As the material used in an anion-exchange method, for separating an objective substance from other substances present together therewith by utilizing the anionic properties of the polypeptide of the present invention, any material can be exemplified without particular restriction so long as it has anion-exchange capacity. The carrier includes, for example, carriers having an anion-exchange group such as diethylaminoethyl (DEAE) group, quaternary ammonium group (e.g. Q group, QAE group, etc.) or the like. More specific examples of the material are packings for anion-exchange chromatography, such as DEAE-MC1 gel (a trade name, Mitsubishi Kasei Corp.), QAE MC1 gel (a trade name, Mitsubishi Kasei Corp.), Wakobeads DEAE gel (a trade name, Wako Pure Chemical Industries, Ltd.), etc.; and materials using a membrane, such as MemSep DEAE (a trade name, Japan Millipore Ltd.). Needless to say, there may be used commercially available materials for chromatography, and materials personally prepared by attaching the above-exemplified anion-exchange group to the surface of a resin or glass container by a conventional method.

The process for measuring a living body component by use of the combined product of the present invention is excellent because it utilizes an anion-exchanger.

For example, for practicing the measuring process of a living body component by utilizing a gel filtration method, a column with a suitable length should be used. Therefore, the employment of a gel filtration method is disadvantageous in that it results in a longer separation time than does the employment of an ion-exchanger. Therefore, when the reduction of the separation time is required, a method using an anion-exchanger such as a HPLC apparatus equipped with a column packed with a packing material for anion-exchange chromatography, an anion-exchange membrane, and a reaction tube having an anion-exchange action is preferably employed. Moreover, gel filtration methods are disadvantageous also in that they are not suitable for separating analytes to be measured in a sample derived from a living body which have a very high molecular weight (size of molecule: about 1,000 Å or more).

A hydrophobic separation method, in some case, causes the following problem: when analytes to be measured in a sample derived from a living body are physiologically active substances having a higher-order structure, such as proteins, the activity of the analyte(s) in the complex is lost owing to the destruction of higher-order structure of the analyte(s) by an organic solvent used in the separation.

On the other hand, the method using an anion-exchanger permits more effective separation of analytes to be measured in a sample derived from a living body, on the basis of the delicate difference in ionicity. Moreover, when the method using an anion-exchanger is employed, the polypeptide of the present invention may be selected from polypeptides various in ionicity, so that analytes to be measured in a sample derived from a living body can be separated at an optimum pH. In addition, since the polypeptide of the present invention has a high water-solubility in itself, there is almost no fear that the introduction of the polypeptide into analytes to be measured in a sample derived from a living body may precipitate the analytes. Therefore, the separation can be stably carried out.

When analytes to be measured in a sample derived from a living body are measured by the measuring process of the present invention, an objective peak due to the analyte(s) can be shifted to a position at which there is no influence of components of serum, urea, etc. Furthermore, the following effect can also be obtained: since the elution positions of complexes containing different analytes to be measured can be made the same by choosing the combined product of the present invention having suitable properties, properly depending on the analytes, the various analytes can be measured using the method using an anion-exchanger (e.g. HPLC) under the same analysis conditions.

In the measuring process according to the present invention, the amount of the detectable substance, the affinity substance, the affinity substance A, or analyte(s) to be measured in a sample derived from a living body contained in the complex or the labeled complex separated by the method using an anion-exchanger is determined by a predetermined method on the basis of the property detectable by some method of the detectable substance (the affinity substance, the affinity substance A, or the analyte(s)). For example, when the property is enzyme activity, the determination is carried out according to a conventional method of EIA, for example, the method described in Tsunehiro Kitagawa, Toshio Nanbara, Akio Tsuji and Eiji Ishikawa "Koso Meneki Sokuteiho", an extra issue No. 31 of Tanpakushitsu Kakusan Koso, pp. 51–63, KYORITSU-SHUPPAN Ltd., published on Sep. 10, 1987, etc. When the detectable substance is a radioisotope, the determination is carried out according to a conventional method of RIA by properly choosing and using a measuring instrument such as GM counter, liquid scintillation counter, well-type counter, counter for HPLC, or the like, depending on the kind and intensity of a radiation emitted by said radioisotope (see, for example, Yuichi Yamamura, "Ikagaku Jikken Koza Vol. 8" 1st ed., NAKAYAMA-SHOTEN Ltd., 1971). When the property is fluorescence-emitting properties, the determination is carried out according to a conventional method of FIA using a measuring instrument such as fluorometer, for example, the method described in Akira Kawano "Zusetsu Keiko-kotai" 1st ed., Soft Science, Inc., 1983, etc. When the property is luminescence-emitting properties, the determination is carried out according to a conventional method using a measuring instrument such as photon counter, for example, the method described in Tsunehiro Kitagawa, Toshio Nanbara, Akio Tsuji and Eiji Ishikawa "Koso Meneki Sokuteiho", an extra issue No. 31 of Tanpakushitsu Kakusan Koso, pp. 252–263, KYORITSU-SHUPPAN Ltd., published on Sep. 10, 1987, etc. When the property is that of absorbing an ultraviolet light, the determination is carried out according to a conventional method using a measuring instrument such as spectrophotometer. When the detectable substance is a substance having properties as spin labels, the determination is carried out according to a conventional method using an electron spin resonance apparatus, for example, the method described in Tsunehiro Kitagawa, Toshio Nanbara, Akio Tsuji and Eiji Ishikawa "Koso Men-eki Sokuteiho", an extra issue No. 31 of Tanpakushitsu Kakusan Koso, pp. 264–271, KYORITSU-SHUPPAN Ltd., published on Sep. 10, 1987, etc.

In the measuring process according to the present invention, the reaction conditions for forming a complex by reacting an analyte(s) to be measured in a sample derived from a living body with the combined product (including the combined products A, B, C and D, etc.) of the present invention and optionally the labeled or unlabeled affinity substance (including the affinity substance A), or the reaction conditions for forming a labeled complex by reacting an analyte(s) to be measured in a sample derived from a living body with labeled analyte and the combined product of the present invention are not particularly limited so long as they do not inhibit the formation of the complex (or the labeled complex). The reaction may be carried out under reaction conditions employed for forming a complex or the like in a conventional method such as EIA, RIA, FIA or affinity chromatography. For example, when a buffer solution is used in the reaction, as the buffer and other reagents, those used in the above conventional methods may be properly chosen. Although the pH at the reaction is not particularly limited so long as it does not inhibit the formation of the complex (or the labeled complex), it is usually 2–10, preferably 5–9.

Although the temperature at the reaction is also not particularly limited so long as it does not inhibit the formation of the complex (or the labeled complex), it is usually 0–50° C., preferably 20–40° C. As to the reaction time, since the time required for the formation of the complex (or the labeled complex) varies depending on the reactivity of the analyte(s) with the combined product of the present invention and the labeled affinity substance or the like, or with the combined product of the present invention and the labeled analyte, the reaction may be properly carried out for several seconds to several hours, depending on properties of these components.

In the HPLC used for practicing the method using an anion-exchanger in the measuring process of the present invention, any apparatus can be used without any particular problem so long as it is usually used in the analysis field and has a constant flow rate. In the measuring process of the present invention using the HPLC, the peak area or peak height is utilized for determining the amount of analyte(s).

A solvent (an eluent) used for separating the complex (or the labeled complex) from free labeled affinity substance, etc. by the method using an anion-exchanger, more specifically HPLC is not particularly limited so long as it neither decomposes the formed complex (or the formed labeled complex) and the like into analyte(s), the labeled affinity substance, etc. nor takes the property detectable by some method away from the affinity substance, the detectable substance or the like, which is contained in the complex (or the labeled complex). Usually, as the solvent, there is preferably used any of buffer solutions which are used in conventional methods such as EIA, RIA, FIA, affinity chromatography, etc. Preferable specific examples of the solvent are buffer solutions having a pH of 2 to 10 prepared by properly choosing the materials described below, depending on properties of the complex (or the labeled complex), the free labeled affinity substance and the like, followed by addition and mixing: for example, buffers such as phosphates, acetates, citrates, Good's buffers, tris (hydroxymethyl)aminomethane, etc.; salts such as sodium chloride, potassium chloride, ammonium sulfate, etc.; polar organic solvents such as methanol, ethanol, isopropanol, acetonitrile, tetra-hydrofuran, etc.; and surfactants.

Proper addition of a suitable surfactant to the eluent permits prevention of tailing of a peak due to the complex (or the labeled complex) and freer adjustment of elution positions of the complex (or the labeled complex), the free labeled affinity substance and the like. The surfactant usable for these purposes is not particularly limited in kind and may be properly chosen depending on properties of the complex (or the labeled complex), the free labeled affinity substance and the like. Preferable examples of the surfactant are cationic surfactants such as n-dodecyltrimethylammonium bromide, 1-laurylpyrimidium chloride, etc.; and amphoteric surfactants such as laurylbetaine, lauramide propylbetaine, coconut oil fatty acid amide propyl-betaine, 2-alkyl-N-carboxymethyl-N-hydroxyethylimidazolium betaine, 2-undecyl-N-carboxymethyl-N-hydroxyethylimidazolium betaine, N-lauroyl-N-methyl-β-alanine sodium, etc. When the surfactant is added to the eluent for the above purposes, the concentration of the surfactant added is not particularly limited so long as it brings about a desired effect. Although the concentration is somewhat varied depending on the kind of the surfactant, it is properly chosen in the range of usually 0.01 to 2%, preferably 0.05 to 1%.

In the measuring process of the present invention, as a measuring method after the separation by HPLC, there is preferably employed the method comprising introducing an effluent from a column of HPLC into a detection section as it is, and directly measuring the amount of the detectable substance (or the affinity substance, or analyte(s) to be measured) contained in the complex (or the labeled complex) in the effluent, which method is described, for example, in Shoji Hara and Akio Tsuji "Newest Liquid Chromatography" 1st ed., pp. 92–104, NANZANDO Ltd., published on Feb. 1, 1978. The reason is that this method permits rapid measurement. In this case, when the property detectable by some method of the affinity substance (or the analyte(s)) or that of the detectable substance in labeled affinity substance or the like (or labeled analyte(s)) is, for example, enzyme activity, a reaction section of so-called post-column method, in which a reagent for measuring the enzyme activity is added to the effluent to react therewith, should of course be provided between the column of HPLC and the detection section. As the reagent for measuring the enzyme activity which is used in the reaction section when the property of the detectable substance (or the affinity substance or the analyte(s)) is the enzyme activity, there may be used a reagent prepared by a conventional method, for example, a method based on the content of Tsunehiro Kitagawa, Toshio Nanbara, Akio Tsuji and Eiji Ishikawa "Koso Men-eki Sokuteiho", an extra issue No. 31 of Tanpakushitsu Kakusan Koso, pp. 51–63, KYORITSU-SHUPPAN Ltd., published on Sep. 10, 1987, etc. Alternatively, there may be properly chosen and used a reagent of a commercially available kit for clinical examination. Also when the property of the detectable substance, the affinity substance or the analyte(s) is other than enzyme activity, a suitable reaction section may be provided between the column of HPLC and the detection section in order to add and react a predetermined reagent for the purpose of increasing the detection sensitivity.

When a plurality of eluents different in components are used in the HPLC used in the measuring process of the present invention, elution may be carried out by either a concentration gradient method (a linear gradient method) or a stepwise method. But the stepwise method is preferable because it is advantageous, for example, in that it can be practiced by easy operations, can reduce the actual analysis time, and gives a sharp objective peak.

The reagent for measuring the analyte according to the present invention comprises a combined product of the polypeptide of the present invention and a substance having affinity for the analyte or a combined product of the maleimide compound and a substance having a SH group and affinity for the analyte, as the essential component. If necessary, said reagent may properly contain, for example, labeled analyte, labeled affinity substance, a buffer, a surfactant, etc. in addition to the combined product. Preferable properties, specific examples and the like of these components are as described above.

The present invention is more concretely explained below with reference to Examples, which are not by way of limitation but by way of illustration.

The abbreviations used in Examples stand for the following.

Ala; alanine, βAla; β-alanine, Ser: serine, Tyr: tyrosine, Asp: aspartic acid, Fmoc: 9-fluorenyl-methoxycarbonyl group, Alko: p-alkoxybenzyl alcohol, tBu: t-butyl group, TFA: trifluoroacetic acid, BOP: benzothiazol-1-yl-oxy-tris (dimethylamino)phosphonium hexafluorophosphate, HOBt: 1-hydroxy-1H-benzotriazole, DMF: N,N-dimethylformamide, DIEA: N,N-diisopropylethylamine.

Example 1

Synthesis of Ala-(Ser($SO_3$H))$_5$-βAla (SEQ ID NO:3) (polypeptide 3)

(1) Synthesis of Fmoc-Ala-(Ser)$_5$-βAla (SEQ ID NO:1)

Using 2.3 g (1.5 mmols in terms of βAla) of Fmoc-βAla-Alko Resin (100 to 200 mesh, mfd. by Watanabe Chemical Industries, Ltd.) as a starting material, Fmoc-Ala-(Ser)$_5$-βAla (SEQ ID NO:1) was synthesized by a solid phase technique according to the method (BOP/HOBt method) described in a reference (J. Org. Chem., 53, 617–624 (1988)).

In detail, Fmoc-βAla-Alko Resin was first treated with piperidine to remove the Fmoc group. To the thus treated resin were added a DMF solution containing a predetermined amino acid in an amount of 3 equivalents per equivalent of βAla on the resin, and BOP, HOBt and DIEA in amounts of 3 equivalents, 3 equivalents and 5.3 equivalents, respectively, per equivalent of βAla on the resin. The predetermined amino acid was introduced by coupling reaction (twice) at room temperature for 2 hours. Amino acids were introduced one after another by repeating the above process. The order of the introduced amino acids was as follows: Fmoc-Ser(tBu) (mfd. by Wako Pure Chemical Industries. Ltd.), Fmoc-Ser(tBu), Fmoc-Ser(tBu), Fmoc-Ser (tBu), Fmoc-Ser(tBu), Fmoc-Ala (mfd. by Wako Pure Chemical Industries. Ltd.).

After the introduction of all the amino acids, the resin was washed with MeOH, followed by adding thereto 20 ml of a TFA-anisole (95:5) mixed solution, and the reaction was carried out with stirring at room temperature for 1 hour to detach the desired polypeptide from the resin and remove the tBu groups (protecting groups for the hydroxyl group of Ser). After completion of the reaction, the resin was filtered off and the filtrate was concentrated under reduced pressure. Ether was added to the concentrate to precipitate the desired compound. The precipitate was collected and then dried in a desiccator to obtain 0.84 g of Fmoc-Ala-(Ser)$_5$-βAla (SEQ ID NO:1).

(2) Synthesis of Ala-(Ser($SO_3$H))$_5$-βAla (SEQ ID NO:3) (polypeptide 3)

In 40 ml of DMF was dissolved 547 mg (0.67 mmol) of the Fmoc-Ala-(Ser)$_5$-βAla (SEQ ID NO:1) synthesized in (1), followed by adding thereto 30 ml of a DMF.$SO_3$ solution [a solution of 2.57 g of DMF-$SO_3$ (mfd. by Fluka Chemika-Biochemica) in 30 ml of a DMF-pyridine (4:1) mixed solution], and the reaction was carried out overnight at 4° C. To the reaction solution was added 30 ml of a DMF.$SO_3$ solution, and the resulting solution was subjected to reaction overnight at 4° C. After completion of the reaction, the reaction solution was added to 400 ml of acetone, and 'the precipitate formed was collected by filtration and dissolved in 40 ml of DMF. To the resulting solution was added 8 ml of piperidine, and the reaction was carried out with stirring at room temperature for 40 minutes to remove the Fmoc group. The reaction solution was added to 500 ml of acetone and the precipitate formed was collected by filtration, washed with acetone and ether, and then dried in a desiccator. The dried precipitate was subjected to anion-exchange chromatography and then gel filtration to obtain 210 mg of Ala-(Ser($SO_3$H))$_5$-βAla (SEQ ID NO:3) (polypeptide 3).

Table 1 shows the results of amino acid analysis and the ion chromatography of this desired compound.

The amino acid analysis was carried out by means of a Wako PTC-amino acid analyzing system (mfd. by Wako Pure Chemical Industries. Ltd.) (hereinafter the same applied).

Example 2

Synthesis of Ala-Tyr($SO_3$H)$_3$-βAla (SEQ ID NO:13) (polypeptide 11)

Using 0.77 g (0.5 mmol) of Fmoc-SAla-Alko Resin as a starting material, predetermined amino acids were introduced with the same reagents by the same procedure as described in Example 1 (1). The order of the introduced amino acids was as follows: Fmoc-Tyr($SO_3$Na) (mfd. by Bachem Feinchemikalien AG), Fmoc-Tyr($SO_3$Na), Fmoc-Tyr($SO_3$Na), Fmoc-Ala.

After the introduction of all the amino acids, the resin was washed with MeOH, followed by adding thereto 50 ml of a DMF-piperidine (4:1) mixed solution, and the reaction was carried out with stirring at room temperature for 1 hour to remove the Fmoc group. The solvent was removed by filtration, after which the resin was washed with MeOH and a mixture of TFA, $H_2O$ and m-cresol (45:5:2) was added. Then, under nitrogen gas stream, the reaction was carried out at 4° C. for 16 hours to detach the desired polypeptide from the resin. The resin was removed from the reaction solution by filtration, and the filtrate was concentrated under reduced pressure, after which the desired compound was precipitated with ether. The precipitate was subjected to anion-exchange chromatography and then gel filtration to obtain 180 mg of Ala-Tyr($SO_3$H)$_3$-βAla (SEQ ID NO:10) (polypeptide 11).

Table 1 also shows the results of amino acid analysis and the ion chromatography of the desired compound.

Example 3

Synthesis of Ala-(Tyr($SO_3$H))5-βAla (SEQ ID NO:13) (polypeptide 14)

(1) Synthesis of Fmoc-Ala-(Tyr)$_5$-βAla (SEQ ID NO:23)

Using 2.3 g (1.5 mmols) of Fmoc-βAla-Alko Resin as a starting material, predetermined amino acids were introduced with the same reagents by the same procedure as described in Example 1 (1). The order of the introduced amino acids was as follows: Fmoc-Tyr(tBu) (mfd. by Watanabe Chemical Industries, Ltd.), Fmoc-Tyr(tBu), Fmoc-Tyr(tBu), Fmoc-Tyr(tBu), Fmoc-Tyr(tBu), Fmoc-Ala.

After the introduction of all the amino acids, the resin was washed with MeOH, followed by adding thereto a mixed solution of TFA, thioanisole and 1,2-ethanediol (95:5:1), and the reaction was carried out with stirring at room temperature for 1 hour to detach the polypeptide from the resin and remove the tBu groups (protecting groups for the hydroxyl group of Tyr). After completion of the reaction, the resin was filtered off and the filtrate was concentrated under reduced pressure. Ether was added to the concentrate to precipitate the desired compound. The precipitate was collected and then dried in a desiccator to obtain 1.71 g of Fmoc-Ala-(Tyr)$_5$-βAla (SEQ ID NO:23).

(2) Synthesis of Ala-(Tyr(SO$_3$H))$_5$-βAla (SEQ ID NO:13) (polypeptide 14)

To a mixture of 0.5 g of the Fmoc-Ala-(Tyr)$_5$-βAla (SEQ ID NO:23) obtained in (1) and 3 ml of DMF was added 15 ml of a DMF.SO$_3$ solution [a solution of 3.2 g of DMF.SO$_3$ in 15 ml of a DMF-pyridine (4:1) mixed solution], and the reaction was carried out overnight at 4° C., after which ether was added to the reaction solution to precipitate the reaction product. The precipitate was dissolved in 10 ml of DMF, followed by adding thereto 2.5 ml of piperidine, and the reaction was carried out with stirring at room temperature for 1 hour. To the reaction solution was added 150 ml of ether, and the precipitate formed was collected by filtration. The precipitate was dissolved in 4 ml of water and the desired compound was isolated by an ODS column liquid chromatography [column: Wakosil $_{10}$C$_{18}$ (2.0φ×25 cm) (mfd. by Wako Pure Chemical Industries. Ltd.); elution conditions: 10 mM AcONa (pH 6.0), 2→60% acetonitrile]. Thus obtained fraction containing the desired compound was treated by gel filtration to obtain 203 mg of Ala-(Tyr(SO$_3$H))$_5$-βAla (SEQ ID NO:13) (polypeptide 14).

Table 1 also shows the results of amino acid analysis and the ion chromatography of this desired compound.

Example 4

Synthesis of sulfated polypeptides (polypeptides 1, 2, 4 to 9, 18, and 20 to 22)

The polypeptides 1, 2, 4 to 9, 18, and 20 to 22 listed in Table 1 were synthesized with the same reagents by the same procedure as described in Example 1. The polypeptide 10 listed in Table 1 was synthesized with the same reagents by the same procedure as described in Example 2.

Fmoc-Ser(tBu)-O-polymer (mfd. by Kokusan Chemical Works, Ltd.) was used as a starting material for synthesizing the polypeptide 6, and Fmoc-Tyr(tBu)-Alko Resin (100 to 200 mesh, mfd. by Watanabe Chemical Industries, Ltd.) was used as a starting material for synthesizing the polypeptides 21 and 22.

Table 1 also shows the results of amino acid analysis and ion chromatography of the thus obtained various polypeptides.

Example 5

Synthesis of sulfated polypeptides (polypeptides 12, 13, 15 to 17, and 19)

The polypeptides 12, 13, 15 to 17, and 19 listed in Table 1 were synthesized with the same reagents by the same procedure as described in Example 3. Fmoc-βAla-Alko Resin (100 to 200 mesh, mfd. by Watanabe Chemical Industries, Ltd.) was used as a starting material for synthesizing the polypeptides 12 and 16, and Fmoc-Tyr(tBu)-Alko Resin (100 to 200 mesh, mfd. by Watanabe Chemical Industries, Ltd.) was used as a starting material for synthesizing the polypeptides 13, 15, 17 and 19.

Table 1 also shows the results of amino acid analysis and ion chromatography of the desired compounds.

Example 6

Synthesis of Ala-(Tyr(PO$_3$H$_2$))$_5$-βAla (SEQ ID NO:22) (polypeptide 23)

Using 780 mg (0.5 mmol) of Fmoc-βAla-Alko Resin as a starting material, predetermined amino acids were introduced with the same reagents by the same procedure as described in Example 1 (1). The order of the introduced amino acids was as follows: Fmoc-Tyr(PO$_3$H$_2$) (mfd. by Novabiochem Corp.), Fmoc-Tyr(PO$_3$H$_2$), Fmoc-Tyr (PO$_3$H$_2$), Fmoc-Tyr(PO$_3$H$_2$), Fmoc-Tyr(PO$_3$H$_2$), Fmoc-Ala.

After the introduction of all the amino acids, the resin was washed with MeOH, followed by adding thereto 50 ml of a DMF-piperidine (4 : 1) mixed solution, and the reaction was carried out with stirring at room temperature for 1 hour to remove the Fmoc group. After completion of the reaction, the resin was collected by filtration and washed with MeOH, and then 20 ml of a mixed solution of TFA, phenol, H$_2$O, thioanisole and ethanediol (33:2:2:2:1) was added. The resulting mixture was subjected to reaction with stirring at room temperature for 1 hour to detach the polypeptide from the resin. After completion of the reaction, the resin was filtered off, and ether was added to the filtrate to precipitate the desired compound. The thus obtained precipitate was subjected to anion-exchange chromatography and then gel filtration to obtain 760 mg of Ala-(Tyr(PO$_3$H$_2$))$_5$-βAla (SEQ ID NO:22) (polypeptide 23).

Table 1 also shows the results of amino acid analysis and the ion chromatography of the desired compound.

Example 7

Synthesis of 4-maleimidobutyryl-Ala-(Tyr(PO$_3$H$_2$))$_5$-βAla (SEQ ID NO:22) (polypeptide 24)

Using 780 mg (0.5 mmol) of Fmoc-βAla-Alko Resin as a starting material, predetermined amino acids were introduced with the same reagents by the same procedure as described in Example 1 (1). The order of the introduced amino acids was as follows: Fmoc-Tyr(PO$_3$H$_2$) (mfd. by Novabiochem Corp.), Fmoc-Tyr(PO$_3$H$_2$), Fmoc-Tyr (PO$_3$H$_2$), Fmoc-Tyr(PO$_3$H$_2$), Fmoc-Tyr(PO$_3$H$_2$), Fmoc-Ala, maleimidobutyric acid.

After the introduction of all the amino acids, the resin was washed with MeOH and treated with a TFA-anisole (95:5) mixed solution to detach the polypeptide from the resin. The resin was filtered off and ether was added to the filtrate to form a precipitate. The precipitate was subjected to an ODS column liquid chromatography [column: Wakosil $_5$C$_{18}$ (2.0φ×25 cm) (mfd. by Wako Pure Chemical Industries. Ltd.); elution conditions: 0.1% TFA, 0→10% acetonitrile] and then gel filtration to obtain 820 mg of 4-maleimidobutyryl-Ala-(Tyr(PO$_3$H$_2$))$_5$-βAla (SEQ ID NO:22) (polypeptide 24).

Table 1 also shows the results of amino acid analysis and the ion chromatography of the desired compound.

TABLE 1

Structures of peptides and results of amino acid analysis and in chromatography

| Peptide No. | Structure of peptide | Results of amino acid analysis Ratio among amino acids | | | | Results of ion chromatography (anion) Number of sulfonic (phosphonic) group per petride | |
|---|---|---|---|---|---|---|---|
| | | Ala: | Ser: | Tyr: | βAla | Found | Calcd. |
| 1 | Ala-Ser(SO$_3$H)-βAla | 1.0 | 1.0 | 0.0 | 1.0 | 1.0 | 1.0 |
| 2 (SEQ ID NO: 2)--; | Ala-[Ser(SO$_3$H)]$_3$-βAla | 1.0 | 3.0 | 0.0 | 1.0 | 3.0 | 3.0 |
| 3 (SEQ ID NO: 3)--; | Ala-[Ser(SO$_3$H)]$_5$-βAla | 1.0 | 5.0 | 0.0 | 1.0 | 5.0 | 5.0 |
| 4 (SEQ ID NO: 4)--; | Ala-[Ser(SO$_3$H)]$_8$-βAla | 1.0 | 7.9 | 0.0 | 0.9 | 8.1 | 8.0 |
| 5 (SEQ ID NO: 5)--; | [Ser(SO$_3$H)]$_8$-βAla | 0.0 | 8.0 | 0.0 | 1.0 | 8.0 | 8.0 |
| 6 (SEQ ID NO: 6)--; | Ala-Ala-Ala-[Ser(SO$_3$H)]$_{10}$ | 3.0 | 10.2 | 0.0 | 0.0 | 10.0 | 10.0 |
| 7 (SEQ ID NO: 7)--; | Ala-[Ser(SO$_3$H)]$_{20}$-βAla | 1.0 | 18.2*) | 0.0 | 0.9 | 20.0 | 20.0 |
| 8 (SEQ ID NO: 8)--; | Ala-[Ser(SO$_3$H)-Ser(SO$_3$H)-Ser(SO$_3$H)-βAla]$_3$ | 1.0 | 8.8 | 0.0 | 2.9 | 9.0 | 9.0 |
| 9 (SEQ ID NO: 9)--; | Ala-[Ser(SO$_3$H)-Ser(SO$_3$H)-βAla]$_3$ | 1.0 | 10.1 | 0.0 | 5.1 | 10.0 | 10.0 |
| 10 | Ala-Tyr(SO$_3$H)-βAla | 1.0 | 0.0 | 1.0 | 1.1 | 1.0 | 1.0 |
| 11 (SEQ ID NO: 10)--; | Ala-[Tyr(SO$_3$H)]$_3$-βAla | 1.0 | 0.0 | 3.0 | 1.0 | 3.0 | 3.0 |
| 12 (SEQ ID NO: 11)--; | Ala-[Tyr(SO$_3$H)]$_4$-βAla | 1.0 | 0.0 | 4.0 | 1.0 | 4.0 | 4.0 |
| 13 (SEQ ID NO: 12)--; | Ala-[Tyr(SO$_3$H)]$_4$ | 1.0 | 0.0 | 4.0 | 0.0 | 4.0 | 4.0 |
| 14 (SEQ ID NO: 13)--; | Ala-[Tyr(SO$_3$H)]$_5$-βAla | 1.0 | 0.0 | 5.0 | 1.0 | 5.0 | 5.0 |
| 15 (SEQ ID NO: 14)--; | Ala-[Tyr(SO$_3$H)]$_5$ | 1.0 | 0.0 | 5.0 | 0.0 | 5.0 | 5.0 |
| 16 (SEQ ID NO: 15)--; | Ala-[Tyr(SO$_3$H)]$_7$-βAla | 1.0 | 0.0 | 5.4**) | 1.0 | 7.0 | 7.0 |
| 17 (SEQ ID NO: 16)--; | Ala-[Tyr(SO$_3$H)]$_7$ | 1.0 | 0.0 | 5.2**) | 0.0 | 7.0 | 7.0 |
| 18 (SEQ ID NO: 17)--; | Ala-[Tyr(SO$_3$H)]$_8$-βAla | 1.0 | 0.0 | 5.3**) | 1.0 | 7.9 | 8.0 |
| 19 (SEQ ID NO: 18)--; | Ala-[Tyr(SO$_3$H)]$_8$ | 1.0 | 0.0 | 5.4**) | 0.0 | 8.0 | 8.0 |
| 20 (SEQ ID NO: 19)--; | Ala-[Tyr(SO$_3$H)]$_{10}$-βAla | 1.0 | 0.0 | 5.2**) | 1.0 | 10.0 | 10.0 |
| 21 (SEQ ID NO: 20)--; | Ala-[Ser(SO$_3$H)]$_8$-[Tyr(SO$_3$H)]$_5$ | 1.0 | 8.0 | 5.0 | 0.0 | 13.0 | 13.0 |
| 22 (SEQ ID NO: 21)--; | [Ser(SO$_3$H)]$_8$-[Tyr(SO$_3$H)]$_5$ | 0.0 | 8.0 | 4.9 | 0.0 | 13.1 | 13.0 |
| 23 (SEQ ID NO: 22)--; | Ala-[Tyr(PO$_3$H$_2$)]$_5$-βAla | 1.0 | 0.0 | 5.0 | 1.0 | 5.0 | 5.0 |
| 24 (SEQ ID NO: 22)--; | 4-Maleimidobutyryl-Ala-(Tyr(PO$_3$H$_2$))$_5$-βAla | 1.0 | 0.0 | 5.0 | 1.0 | 5.0 | 5.0 |

*)The value was rather low for 20 Ser residues. From the result of ion chromatography, the structure is considered correct.
**)Less than six of the Tyr residues could be measured. It can be speculated that this result was brought about by the low water-solubility of the amino acid.

Example 8

Investigation on the elution positions of anionic polypeptides in the case of an anion-exchange column

[Samples]

Aqueous solutions containing 5 mg/ml of the polypeptides 1 to 24, respectively, obtained in Examples 1 to 7 were used as samples.

There were also prepared, as samples, aqueous solutions containing as a reference standard compound 5 mg/ml of (Asp)$_9$-βAla (hereinafter abbreviated as "Asp 9"; personally prepared by the BOP/HOBt method), a poly(aspartic acid) having an average molecular weight of 6,000 (hereinafter abbreviated as "Asp6K"; mfd. by Sigma Chemical Co.) or a poly(aspartic acid) having an average molecular weight of 50,000 (hereinafter abbreviated as "pAsp"; mfd. by Sigma Chemical Co.), respectively.

[Analysis Conditions]

| | |
|---|---|
| Column: | POROS-DEAE (4.6 φ × 10 mm, mfd. by Perseptive Biosystems). |
| Eluent A: | 50 mM phosphate buffer (pH 7.6). |
| Eluent B: | 50 mM phosphate buffer (pH 7.6, containing 5 M NaCl). |
| Flow rate: | 1 ml/min. |
| Detection: | for the polypeptides containing one or more sulfated serine residues: UV 220 nm, for the polypeptides containing one or more sulfated tyrosine residues: UV 260 nm, for the polypeptides containing phosphated tyrosine residues: UV 260 nm. |

-continued

| | | |
|---|---|---|
| Gradient condition: | 0 → 5 min. | A = 100% |
| | 5 → 30 min. | B = 0 → 100% |
| | 30 → 35 min. | B = 100% |

[Measuring Procedure]

There was analyzed 20 μl of each sample by HPLC under the above-mentioned conditions.

[Results]

FIG. 1 shows salt concentrations required for the elution of the individual polypeptides (hereinafter abbreviated as "eluting salt concentration"). In FIG. 1, ● shows a salt concentration at the top of elution peak, ⊢⊣ a shows a salt concentration range between the start and end of elution, i.e., a peak width. The Nos. and marks on the axis of abscissa show the kind of the polypeptides (the polypeptide Nos. and abbreviations in Table 1).

The following can be seen from the results shown in FIG. 1.

(i) Increasing the number of the acid residues (sulfonic groups or phosphonic groups) results in an increased eluting salt concentration.

(ii) Polypeptide 3 (number of sulfuric acid residues: 5) and polypeptide 11 (number of sulfuric acid residues: 3) are equal to Asp 9 in eluting salt concentration. Polypeptide 6 (number of sulfuric acid residues: 10), polypeptide 8 (number of sulfuric acid residues: 9), polypeptide 9 (number of sulfuric acid residues: 10), polypeptides 12 and 13 (number of sulfuric acid residues: 4) and polypeptides 14 and 15 (number of sulfuric acid residues: 5) are equal to Asp6K and pAsp in eluting salt concentration. In other words, the polypeptides of the present invention bring about an effect equal to that of the conventional polypeptides having carboxylic acid residues (they are equal to the conventional polypeptides in the strength of holding by an anion-exchange column) even if they have a shorter chain length (a smaller number of amino acid residues) than do the conventional polypeptides.

(iii) The strength of holding by an anion-exchange column varies depending on the kind of the acid residues derived from a strong acid, the kind of amino acid residues into which the acid residues have been introduced, properties of a packing for column, etc. For example, comparison between the results for polypeptides 2 to 9 containing sulfated serine residues and the results for polypeptides 10 to 20 containing one or more sulfated tyrosine residues indicates that when the number of acid residues derived from a strong acid is the same in the former and the latter polypeptides, the polypeptides containing one or more sulfated tyrosine residues have a higher eluting salt concentration. The reason is guessed as follows: since a base material for the packing used in the present example is somewhat hydrophobic, the polypeptides containing tyrosine residues having a benzene ring are more easily held by the column, so that their apparent eluting salt concentration is higher. Comparison between the results for polypeptides 3 and 14 containing 5 sulfuric acid residues and the results for polypeptides 23 and 24 containing 5 phosphoric acid residues indicates that the polypeptides containing sulfuric acid residues have a higher eluting salt concentration. From the above results, it can be seen that a polypeptide having an arbitrary eluting salt concentration can be chosen by properly choosing the kind and number of acid residues to be introduced, the kind of constituent amino acid residues, the kind of a packing for column, etc.

(iv) Even if the kind and number of amino acid residues into which acid residues derived from a strong acid have been introduced are the same and the kind and number of the acid residues are the same, the strength of holding of such polypeptides by an anion-exchange column varies depending on the presence of other amino acid residues in the polypeptides. For example, from the results for polypeptides 12 to 19 containing sulfated tyrosine residues, it can be seen that the eluting salt concentration varies depending on the presence of a β-alanine residue (the introduction of a β-alanine residue decreases the eluting salt concentration) even if the number of sulfated tyrosine residues is the same. Thus, it can be seen that a polypeptide having an arbitrary eluting salt concentration can be prepared by introducing a suitable amino acid residue in addition to the amino acid residues having the acid residue introduced thereinto.

(v) From the results for pAsp-1 and pAsp-2 (pAsp's in different production lots) as comparative examples, the following can be seen: depending on the production lot, the conventional polypeptides having carboxylic acid residues vary in eluting salt concentration, in other words, the tailing of an objective peak varies, namely, it is difficult to obtain a polypeptide having a uniform molecular weight. By contrast, the polypeptide of the present invention is free from such a problem in pAsp because it can easily be obtained as a polypeptide with a uniform molecular weight by peptide synthesis.

Example 9

Preparation of an antibody-sulfated polytyrosine combined product
(1) Preparation of 4-(p-maleimidophenyl)butyryl-Ala-(Tyr(SO$_3$H))$_8$-βAla (SEQ ID NO:17)

In 500 μl of 0.1 M phosphate buffer (pH 7.0) was dissolved 1 mg of the Ala-(Tyr(SO$_3$H))$_8$-βAla (SEQ ID NO:17) prepared in Example 4, followed by adding thereto 1.2 mg of sulfosuccinimidyl-4-(p-maleimidophenyl) butyrate (mfd. by Pierce Chemical Co.), and the reaction was carried out at 37° C. for 3 hours. The reaction solution was treated with a Superdex peptide column (16 mm ID×30 cm, mfd. by Pharmacia AB) to remove the excess reagents, whereby an aqueous solution of 0.84 mg of 4-(p-maleimidophenyl)butyryl-Ala-(Tyr(SO$_3$H))B-βAla (SEQ ID NO:17) was obtained (yield: 75%).

(2) Preparation of Fab' fragment

By a conventional method, 10 mg of anti-AFP monoclonal antibody A4-4 (hereinafter abbreviated as "AFP-A4-4"; available from Wako Pure Chemical Industries, Ltd.) was treated into F(ab')$_2$ fragment (5 mg, yield 80%). Then, the F(ab')$_2$ fragment was treated into Fab' fragment (hereinafter abbreviated as "AFP-A4-4.Fabl") (3.1 mg, yield 62%) by a conventional method.

(3) Preparation of a combined product of Ala-(Tyr(SO$_3$H))$_8$-βAla (SEQ ID NO:17) and AFP-A4-4.Fab'

In 0.1 M phosphate buffer (pH 7.0), 3.1 mg of the 4-(p-maleimidophenyl)butyryl-Ala-(Tyr(SO$_3$H))$_8$-βAla (SEQ ID NO:17) obtained in (1) above and 3.1 mg of the AFP-A4-4.Fab' obtained in (2) above were reacted at 4° C. for 16 hours. The reaction solution was charged into a Superdex 200 pg column (26 mm ID×60 cm, mfd. by Pharmacia AB) to remove the excess 4-(p-maleimidophenyl)butyryl-Ala-(Tyr(SO$_3$H))$_8$-βAla (SEQ ID NO:17). Then, the residue was treated with a DEAE TOYOPEARL column (10 mm ID×2 cm, mfd. by Tosoh Ltd.) and the adsorbed fraction was recovered to obtain 1 mg of a combined product of Ala-(Tyr(SO$_3$H))8-βAla (SEQ ID NO:17) and AFP-A4-4.Fab' (yield: 15%).

Example 10

Preparation of an antibody-sulfated polytyrosine combined product
(1) Preparation of 4-(p-maleimidophenyl)butyryl-Ala-(Tyr(SO$_3$H))$_8$ (SEQ ID NO:18)

In 3 ml of DMF was dissolved 25 mg of the Ala-(Tyr(SO$_3$H))8 (polypeptide 19) prepared in Example 4, followed by adding thereto 10 mg of sulfosuccinimidyl-4-(p-maleimidophenyl) butyrate (mfd. by Pierce Chemical Co.), and the reaction was carried out at room temperature for 1 hour. The reaction mixture was treated with an ODS column [column: Wakosil 5C18 (2.0φ×25 cm) (mfd. by Wako Pure Chemical Industries, Ltd.); elution conditions: 50 mM ammonium acetate pH 6, 2→60% acetonitrile]. The thus obtained fraction containing the desired compound was concentrated to dryness to obtain 26.5 mg of 4-(p-maleimidophenyl)butyryl-Ala-(Tyr(SO$_3$H))$_8$ (SEQ ID NO:18) (yield: 95%).

NMR data of the obtained 4-(p-maleimido-phenyl) butyryl-Ala-(Tyr(SO$_3$H))$_8$ (SEQ ID NO:18) are shown below:

1H-NMR (270 MHz, DMSO-d$_6$) δppm: 7.16 (s, 2H, maleimide proton)

Comparison with the result obtained in Example 9 (1) indicates that according to the method described above, a polypeptide having a maleimide group introduced into the N-terminus can be obtained in higher yield.

It was also found that when stored at 15° C. or lower, the 4-(p-maleimidophenyl)butyryl-Ala-(Tyr(SO$_3$H))$_8$ (SEQ ID NO:18) obtained by the method described above can be stably stored without degradation. Thus, this compound was found to be more easily usable than the compound obtained by the method described in Example 9 (1) which was in the form of an aqueous solution and was almost completely degradable in about 24 hours.

(2) Preparation of Fab' fragment

By a conventional method, 30 mg of anti-AFP monoclonal antibody A4-4 (hereinafter abbreviated as "AFP-A4-4"; available from Wako Pure Chemical Industries, Ltd.) was treated into F(ab')$_2$ fragment (16 mg, yield 80%). Then, the F(ab')$_2$ fragment was treated into Fab' fragment (hereinafter abbreviated as "AFP-A4-4.Fab'") (11.1 mg, yield 70%) by a conventional method.

(3) Preparation of a combined product of Ala-(Tyr(SO$_3$H))$_8$ (SEQ ID NO:18) and AFP-A4-4.Fab'

In 50 mM phosphate buffer (pH 6.5), 1 mg of the 4-(p-maleimidophenyl)butyryl-Ala-(Tyr(SO$_3$H))$_8$ (SEQ ID NO:18) obtained in (1) above and 11.1 mg of the AFP-A4-4.Fab'obtained in (2) above were reacted at 4° C. for 16 hours. The reaction solution was fractionated by use of a POROS DEAE column (6 mm ID×1 cm, mfd. by Perseptive Biosystems) to obtain 6 mg of a combined product of Ala-(Tyr(SO$_3$H))$_8$ (SEQ ID NO:18) and AFP-A4-4.Fab' (yield: 60%).

From comparison between this result with the result obtained in Example 9 (3), it can be seen that by use of the polypeptide having a maleimide group introduced into the N-terminus which was obtained in Example 10 (1), a combined product of the polypeptide of the present invention and Fab' can be efficiently obtained.

Although not apparent, the reason is guessed as follows: in Example 9 (1), free sulfosuccinimidyl-4-(p-maleimidophenyl) butyrate was removed using the Superdex peptide column, while in Example 10 (1), the removal was carried out using the ODS column. In detail, the following conjecture is given: since the difference in molecular weight between the polypeptide having a maleimide group introduced thereinto of the present invention and free sulfosuccinimidyl-4-(p-maleimidophenyl) butyrate was small, they could not be sufficiently separated from each other by use of the Superdex peptide column, so that free sulfosuccinimidyl-4-(p-maleimidophenyl) butyrate reacted with Fab', resulting in a low yield of the combined product of Ala-(Tyr(SO$_3$H))$_8$-βAla (SEQ ID NO:17) and AFP-A4-4.Fab'.

Example 11

Investigation on the elution positions of combined products of an anionic polypeptide and an antibody in anion-exchange chromatography

[Samples]

Combined products of each of the various anionic polyp eptides listed in Table 1 and AFP-A4-4.Fab'were prepared with the same reagents by the same procedure as described in Example 9. Aqueous solutions containing 1 mg/ml of each combined product were used as samples. Since polypeptide 24 had a maleimide group attached to the N-terminus, it was combined with AFP-A4-4.Fab' as it was without modification with 4-(p-maleimidophenyl) butyrate.

As a reference standard compound, each of commercially available pAsp's (in two lots) was made into a combined product with AFP-A4-4.Fab' by use of the same reagents by the same procedure as described in Example 9. Aqueous solutions containing 1 mg/ml of the thus obtained combined products, respectively, were prepared as samples.

No desired combined product of polypeptide 22 and AFP-A4-4.Fab' could be obtained. The reason is guessed as follows: when an anionic amino acid residue is present at the N-terminus of a polypeptide, the efficiency of combination of the polypeptide with an antibody (more exactly, the combination of the polypeptide with a crosslinking agent) is decreased by a cause relating to electric charge.

[Analysis conditions and measuring procedure]

Analysis and measurement were carried out in the same manner as described in Example 8 except that the detection was carried out at UV 280 nm in all cases.

[Results]

Figure 2:
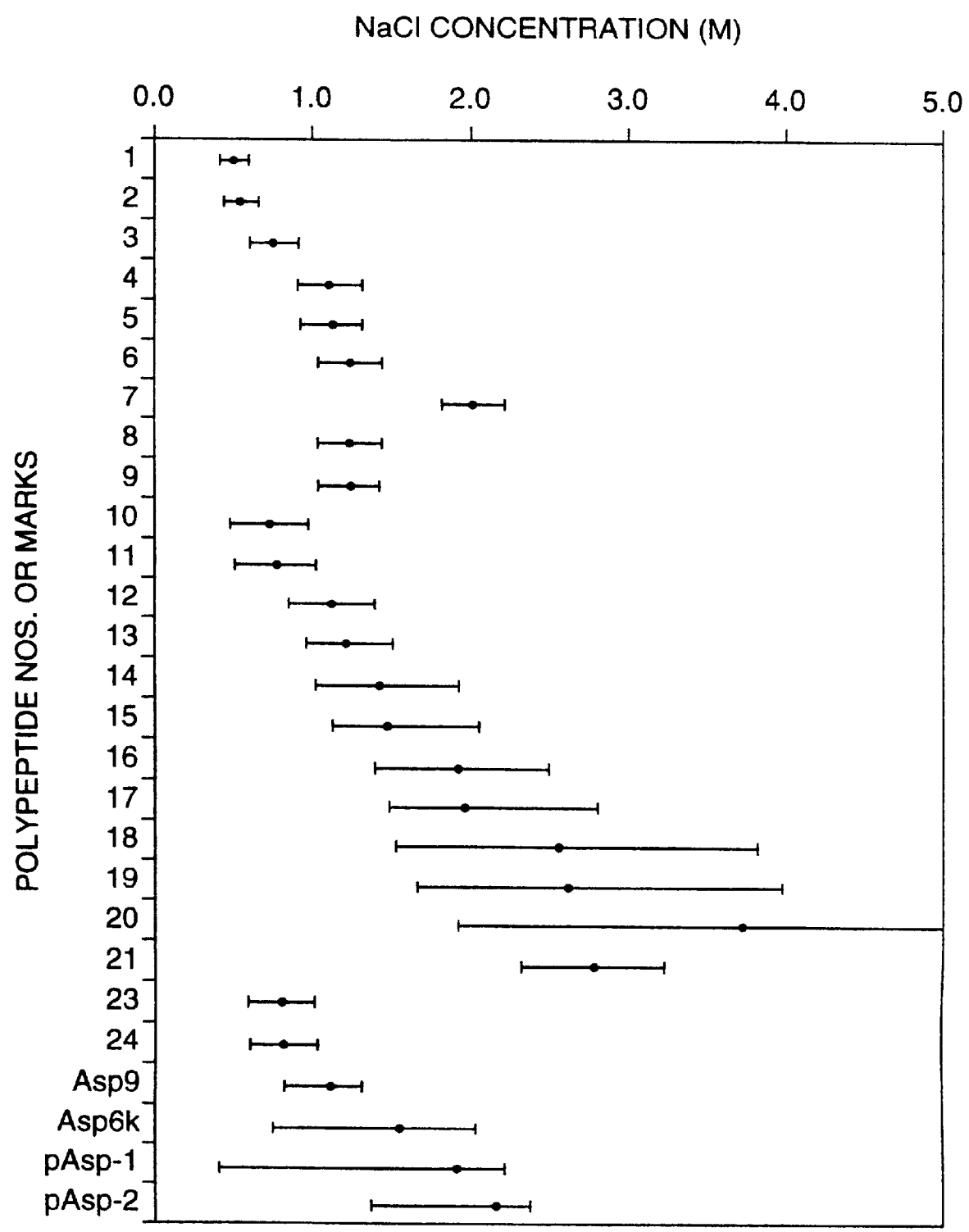
FIG. 2 shows elution positions of combined products of Fab' fragment as antibody and an anionic polypeptide by HPLC using an anion-exchange column obtained in Example 11.

FIG. 2 shows the eluting salt concentrations and the peak widths of the combined products of each of the various polypeptides and AFP-A4-4.Fab'. In FIG. 2, ● shows a salt concentration at the top of elution peak, ⊢─┤ shows a salt concentration range between the start and end of elution, i.e., a peak width. The Nos. and marks on the axis of abscissa show the kind of the polypeptides (the polypeptide Nos. and abbreviations in Table 1).

The following can be seen from the results shown in FIG. 2.

(i) Owing to the combination with the antibody, the eluting salt concentration is a little lower than that of the polypeptide alone, but the interrelation among the eluting salt concentrations of the various polypeptides and the interrelation between the eluting salt concentrations of the polypeptides and those of the pAsp's are the same as the interrelations determined in Example 8.

(ii) When analysis for a serum component was carried out under the analysis conditions described in Example 8 by use of a POROS-DEAE (4.6φ×10 mm, an anion-exchange column), the salt concentration at the top of an elution peak due to a substance present in the serum together with the serum component is near 0.3 M (not shown in FIG. 2). From this fact, it can be found that when the combined product of polypeptide 1 (the number of sulfuric acid residues: 1) and the antibody is used as a separation-improving substance, an objective peak overlaps with the peak due to the substance present in the serum, resulting in a decreased precision of measurement (analysis). The results shown in FIG. 2 suggest that also when the combined product of the antibody and polypeptide 2 (the number of sulfuric acid residues: 3), polypeptide 10 (the number of sulfuric acid residues: 1) or polypeptide 11 (the number of sulfuric acid residues: 3) is used as a separation-improving substance, the precision of measurement (analysis) is somewhat decreased by the influence of the substance present in the serum though the decrease is not so large as that caused in the case of polypeptide 1.

Since a base material for POROS-DEAE, i.e., the packing used in the present example is somewhat hydrophobic, the combined products of the antibody and each of polypeptides 10 to 20 having one or more sulfated tyrosine residues have a higher apparent eluting salt concentration than do the combined products of the antibody and each of the polypeptides having one or more sulfated serine residues. Accordingly, the apparent eluting salt concentration of the combined product of the antibody and polypeptide 10 which contains only one sulfuric acid residue but contains a tyrosine residue is substantially the same as that of the combined product of the antibody and polypeptide 2 having three sulfated serine residues.

However, when the same experiment as above is carried out except for using a packing obtained from a hydrophilic base material, in place of the packing used in the above experiment, the following is anticipated: the apparent eluting salt concentration of the combined product of the antibody and polypeptide 10 having only one sulfated tyrosine residue is substantially the same as that of the combined product of the antibody and polypeptide 1 containing only one sulfated serine residue, so that an objective peak overlaps with a peak due to the substance present in serum, resulting in a decreased precision of measurement (analysis).

From the results described above, it can be seen that a polypeptide having at least 3, preferably 4 or more, more preferably 5 or more acid residues derived from a strong acid is preferable as a separation-improving substance.

Example 12

Investigation on the stability of a polypeptide containing sulfated serine residues and a polypeptide containing sulfated tyrosine residues in an aqueous solution Each of Ala-(Ser(SO$_3$H))$_8$-βAla (SEQ ID NO:4) (polypeptide 4) and Ala-(Tyr(SO$_3$H))$_5$-βAla (SEQ ID NO:13) (polypeptide 14) was stored at 40° C. in a buffer solution having a pH of 6 to 10, whereby their stability was investigated.

[Samples]

As samples, there were used solutions prepared by dissolving each of polypeptides 4 and 14 in each of the following buffer solutions to a final concentration of 1 mg/ml:

Buffer Solutions:

| pH 6.0 | 2-morpholinoethanesulfonic acid (MES), |
| pH 7.0 | 3-morpholinopropanesulfonic acid (MOPS), |
| pH 8.0 | N-tris(hydroxymethyl)methyl-3-aminopropane-sulfonic acid (TAPS), |
| pH 9.0 | TAPS, |
| pH 10.0 | N-cyclohexyl-2-hydroxy-3-aminopropane-sulfonic acid (CAPSO). |

The concentrations of all the buffer solutions were adjusted to 50 mM.

[Storing Method]

Each sample was stored at 40° C. for predetermined numbers of days.

[Results]

The polypeptide remaining rate (%) in each sample was determined on the 6th and 19th days of storage on the basis of the peak area value of the polypeptide in the sample immediately after the preparation and that after the predetermined number of days of storage, which had been determined under the analysis conditions described in Example 8 by the procedure described therein.

Figure 3:
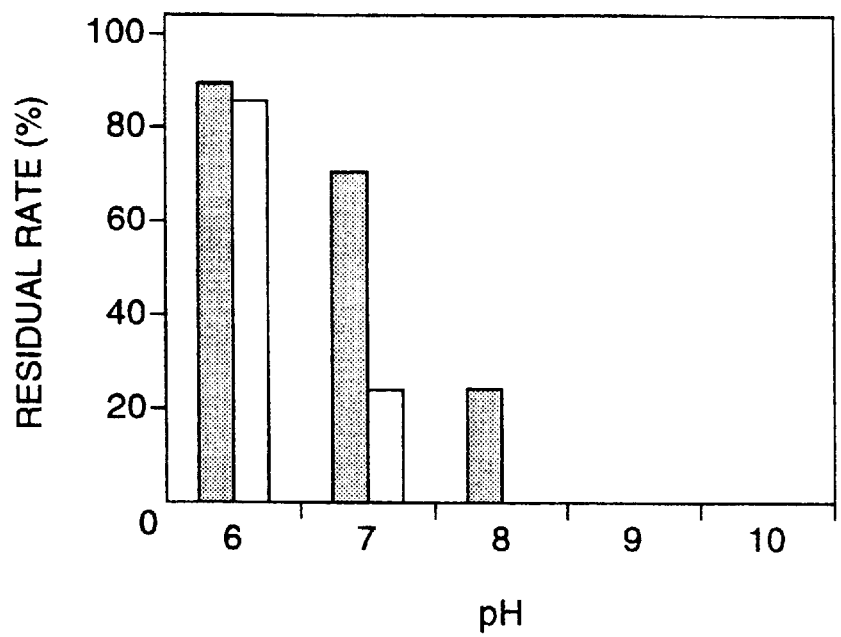
FIG. 3 shows data on the storage stability of a polypeptide having sulfated serine residues in solutions different in pH, which were obtained in Example 12.
Figure 4:
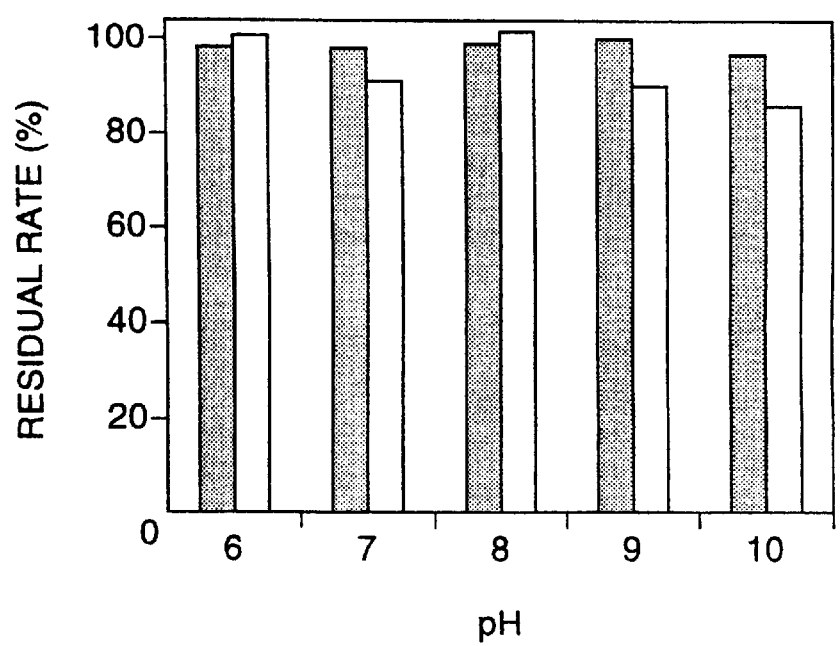
FIG. 4 shows data on the storage stability of a polypeptide having sulfated tyrosine residues in solutions different in pH, which were obtained in Example 12.

FIG. 3 and FIG. 4 show the measurement results obtained for polypeptide 4 and those obtained for polypeptide 14, respectively. In each of FIGS. 3 and 4, the dark bars and the blank bars show the results obtained from each sample on the 6th day and the 19th day, respectively, of storage.

The results shown in FIG. 3 indicate that the degradation of polypeptide 4 is accelerated with an increase of the pH at the storage, and that 10% or more of polypeptide 4 is degraded after 16 days of the storage even at pH 6 at which polypeptide 4 is most stable.

On the other hand, the results shown in FIG. 4 indicate that polypeptide 14 is stable at all the pH values.

From the above results, it can be seen that the sulfonic groups introduced into the tyrosine residues are less susceptible to the influence of pH and hence more stable than the sulfonic groups introduced into the serine residues, namely, the former has a property preferable to that of the latter when used in a separation-improving substance.

Example 13

Measurement of thyroid stimulating hormone (TSH)

[Preparation of peroxidase-labeled anti-TSH antibody Fab' fragment]

Anti-TSH antibody (hereinafter abbreviated as "TSH-1"; available from Wako Pure Chemical Industries, Ltd.) was treated into Fab' fragment by a conventional method. Peroxidase (available from TOYOBO, Co., Ltd.) was introduced into the Fab' fragment by a conventional method to prepare peroxidase-labeled anti-TSH antibody Fab' fragment (hereinafter abbreviated as "TSH-1.Fab'-POD").

[Antibody solution 1]

As antibody solution 1, 50 mM MOPS buffer (pH 7.5) containing 5 nM TSH-1.Fab'-POD was prepared.

[Antibody solutions 2]

Anti-TSH monoclonal antibody which had been confirmed to be different in epitope from TSH-1 (hereinafter abbreviated as "TSH-2"; available from Wako Pure Chemical Industries, Ltd.) was treated into Fab' fragment (hereinafter abbreviated as "TSH-2-Fab'"). Combined products of TSH-2-Fab' and each of Ala-(Tyr(SO$_3$H))$_5$-βAla (SEQ ID NO:13) (polypeptide 14) and Ala-(Ser(SO$_3$H))5-βAla (SEQ ID NO:3) (polypeptide 3) were prepared by the same procedure as described in Example 9 (3).

As antibody solutions 2, 50 mM MOPS buffer solutions containing 50 nM of each of the combined products were prepared.

[Sample]

As a sample, there was used a solution prepared by adding commercially available TSH (available from Genzyme Diagnostics) to 50 mM MOPS buffer (pH 7.5, containing 0.5% bovine serum albumin) to a concentration of 70 pM.

[Use conditions of HPLC]

| Column: | 0.46 φ × 1.0 cm. |
| Packing: | POROS-DEAE gel (a trade name, Perseptive Biosystems). |
| Eluent A: | 50 mM MOPS buffer (pH 7.5). |
| Eluent B: | 50 mM MOPS buffer (pH 7.5, containing 3 M NaCl). |
| Substrate solution: | a 25 mM aqueous solution of 4-N-acetylaminophenol (mfd. by DOJINDO LABORATORIES). |
| Flow rate: | eluent A + eluent B; 1.0 ml/min, the substrate solution; 0.1 ml/min. |
| Reaction section: | 0.025 φ × 1,000 cm (maintained at 60° C.). |
| Detection: | Fluorescence was measured at an excitation wavelength of 328 nm and an emission wavelength of 432 nm. |
| Gradient: | 0 → 10 min.   B = 0 → 100%. |

[Measuring procedure]

With 100 μl of antibody solution 1 were mixed 50 μl of the sample and 50 μl of each antibody solution 2, and the resulting mixture was allowed to stand at 25° C. for 30 minutes, after which 10 μl of the mixture was subjected to measurement (analysis) by HPLC under the above conditions.

[Results]

As a result of the HPLC analysis, the salt concentrations (sodium chloride concentrations) for elution of various substances was found to be as follows:

TSH-1.Fab'-POD, and a complex of TSH-1.Fab'-POD and TSH: 0 to 0.1 M.

a complex of TSH-1.Fab'-POD, TSH, and the combined product of TSH-2-Fab' and Ala-(Tyr(SO$_3$H))$_5$-βAla (SEQ ID NO:13) (polypeptide 14): 0.5 to 1.2 M.

a complex of TSH-1.Fab'-POD, TSH, and the combined product of TSH-2-Fab' and Ala-(Ser(SO$_3$H))$_5$-βAla (SEQ ID NO:3) (polypeptide 3): 0.25 to 0.45 M.

From the above results, it can be seen that the complexes containing the analyte to be measured can be more certainly separated from the free POD-labeled antibody present therewith by using any of the combined products of the sulfated polypeptide and the antibody, and that the elution position of an objective complex can be freely adjusted by properly choosing the kind of the sulfated polypeptide.

It was also found that by utilizing a peak due to the complex having the sulfated polypeptide attached thereto, satisfactory calibration curve for TSH in the sample can be obtained, namely, the amount of TSH can be determined.

Example 14

Measurement of AFP using a combined product of Fab' and an anionic polypeptide

[Preparation of peroxidase-labeled anti-AFP antibody Fab' fragment]

Anti-AFP antibody WA-1 (hereinafter abbreviated as "AFP-WA-1"; available from Wako Pure Chemical Industries, Ltd.) different in epitope from AFP-A4-4 was treated into Fab' fragment by a conventional method. Peroxidase (available from TOYOBO Co., Ltd.) was attached to the Fab' fragment by a conventional method to prepare peroxidase-labeled anti-AFP antibody Fab' fragment (hereinafter abbreviated as "AFP-WA-1-Fab'-POD").

[Reagents]

As reagents, there were prepared MOPS buffer solutions (pH 7.5) containing 200 nM of a predetermined combined product among the combined products prepared in Example 11, i.e., the combined products of AFP-A4-4.Fab' and each of the anionic polypeptides listed in Table 1, 100 nM of AFP-WA-lFab'-POD and 0.2 (w/v) of a poly(vinyl alcohol) (mfd. by Aldrich Chemical Co.).

[Sample]

As a sample, there was used a solution prepared by dissolving commercially available AFP in 50 mM MOPS buffer (pH 7,5, containing 0.2 (w/v)% poly(vinyl alcohol)) to a concentration of 100 ng/ml.

[HPLC conditions]

| | |
|---|---|
| Column: | POROS-DEAE (4.6 φ × 10 mm). |
| Eluent A: | 50 mM MOPS buffer (pH 7.5). |
| Eluent B: | 50 mM MOPS buffer (pH 7.5, containing 3 M NaCl). |
| Substrate solution: | 50 mM MOPS buffer (pH 7.5, containing 90 mM 4-N-(4-carbobutyryl)aminophenol and 20 mM H$_2$O$_2$). |
| Flow rate: | eluent A + eluent B; 1 ml/min, the substrate solution; 0.1 ml/min. |
| Reaction section: | 0.025 φ × 1,000 cm. |
| Temperature: | 60° C. |
| Detection: | Fluorescence was measured at an excitation wavelength of 328 nm and an emission wavelength of 432 nm. |
| Gradient: | the same as in Example 8. |

[Measuring Procedure]

With 100 μl of each reagent was mixed 10 μl of the sample, and the reaction was carried out at 8° C. for 10 minutes, after which 20 μl of the reaction mixture was analyzed by HPLC under the above conditions.

[Results]

Figure 5:
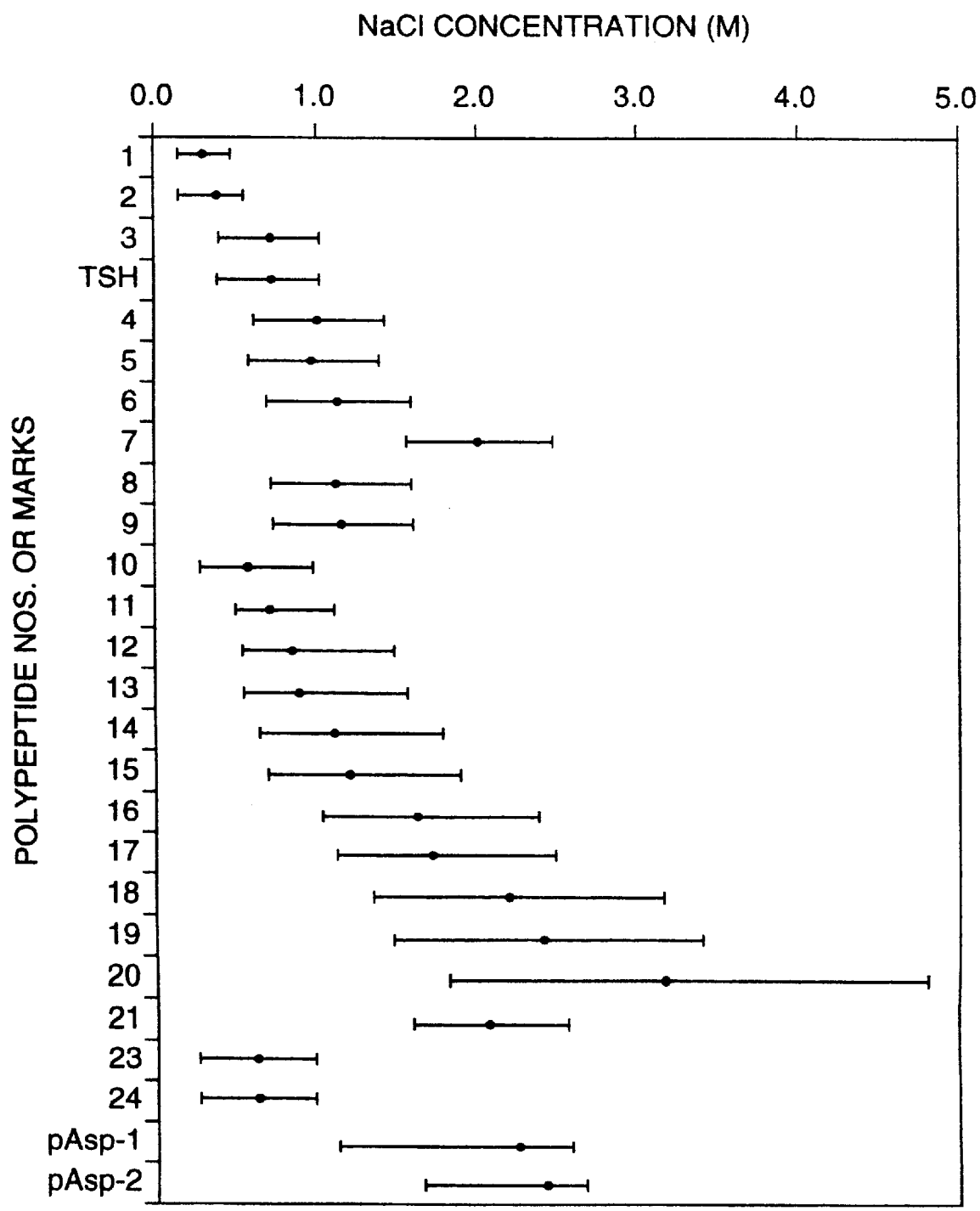
FIG. 5 shows elution positions of various antigen-antibody complexes by HPLC using an anion-exchange column obtained in Example 14.

FIG. 5 shows the eluting salt concentrations and the peak widths of complexes of the combined product of each of the various polypeptides and AFP-A4-4.Fab', AFP-WA-1.Fab'-POD and AFP (antigen-antibody complexes). In FIG. 5, ● shows a salt concentration at the top of elution peak, ⊢⊣ shows a salt concentration range between the start and end of elution, i.e., a peak width. The Nos. and marks on the axis of abscissa show the kind of the polypeptides (the polypeptide Nos. and abbreviations in Table 1).

The following can be seen from the results shown in FIG. 5.

(i) The eluting salt concentrations (the elution positions) of the antigen-antibody complexes vary depending on the kind of the polypeptide attached to AFP-A4-4.Fab'. The order of elution of the antigen-antibody complexes was the same as the order of elution of the combined products of AFP-A4-4.Fab' and each polypeptide (see Example 11 and FIG. 2). These results indicate that the eluting salt concentration of an objective antigen-antibody complex can be properly determined by choosing the kind of the polypeptide properly.

(ii) Since the eluting salt concentration of free AFP-WA-1.Fab'-POD was 0 to 0.1 M, the free AFP-WA-1.-Fab'-POD and the antigen-antibody complex could be completely separated from each other by using any of the polypeptides. Particularly when any of polypeptides 4 to 9 and polypeptides 11 to 21 is used, the eluting salt concentration of the antigen-antibody complex can be adjusted to 0.3 M or more, so that the influence of the substance present in serum together with AFP can be certainly avoided by use of any of these polypeptides as a separation-improving substance.

As previously described, a base material for POROS-DEAE, the packing used in the present example is somewhat hydrophobic, so that the antigen-antibody complexes formed from the combined products of the antibody and each of polypeptides 10 to 20 having one or more sulfated tyrosine residues have a higher apparent eluting salt concentration than do those formed from the combined products of the antibody and each of the polypeptides having one or more sulfated serine residues. Accordingly, the apparent eluting salt concentration of the antigen-antibody complex formed from the combined product of the antibody and polypeptide 10 which has only one sulfuric acid residue but has a tyrosine residue is substantially the same as that of the antigen-antibody complex formed from the combined product of the antibody and polypeptide 2 having three sulfated serine residues.

However, when the same experiment as above is carried out except for using a packing obtained from a hydrophilic base material, in place of the packing used in the above experiment, the following is anticipated: the apparent eluting salt concentration of the antigen-antibody complex formed from the combined product of the antibody and polypeptide 10 having only one sulfated tyrosine residue is substantially the same as that of the antigen-antibody complex formed from the combined product of the antibody and polypeptide 1 containing only one sulfated serine residue, so that an objective peak overlaps with a peak due to the substance present in serum together with AFP, resulting in a decreased precision of measurement (analysis).

(iii) From the above results, it is considered that when a polypeptide is used as a separation-improving substance, the number of acid residues derived from a strong acid in the polypeptide is 3 to 20, preferably 4 to 30, more preferably 5 to 15 (the presence of a large number of the acid residues is not preferable for the measurement because the eluting salt concentration in elution from a column becomes too high).

(iv) Two or more substances having similar structures (e.g. two or more substances different only in a part of a structure such as sugar chain structure, isozymes, two or more antibodies capable of recognizing differents epitopes of an antigen) can be separated and measured by choosing a combination of two or more polypeptides different in eluting salt concentration (e.g. a combination of any of polypeptides 4 to 7, 8, 9, 11 to 14 and any of polypeptides 7 and 16 to 21) and using combined products obtained by attaching each of the two or more polypeptides to a suitable affinity substance.

(v) The results obtained by using each of pAsp-1 and pAsp-2 (pAsp's in different production lots) as a polypeptide suggested that the conventional polypeptides having carboxylic acid residues involve the following problem: depending on the production lots, the conventional polypeptides vary in eluting salt concentration, so that the tailing of an objective peak varies, namely, it is difficult to obtain a polypeptide having a uniform molecular weight. By contrast, the polypeptide of the present invention is free from such a problem in pAsp because it can easily be obtained as a polypeptide with a uniform molecular weight by peptide synthesis.

There were mixed 100 μl of the antibody solution 1, 50 μl of the sample and 50 μl of the antibody solution 2 [containing a combined product of TSH-2-Fab' and Ala-(Ser(SO$_3$H))$_5$-βAla (SEQ ID NO:3) (polypeptide 3)] which had been prepared in Example 13. After standing at 25° C. for 30 minutes, 20 μl of the resulting mixture was subjected to measurement (analysis) by HPLC under the conditions described above. As a result, an objective antigen-antibody complex was eluted at the eluting salt concentration of an antigen-antibody complex formed when measurement of (analysis for) AFP was carried out using polypeptide 3 (data on the eluting salt concentration are also shown at a position corresponding to the abbreviation TSH on the axis of abscissa in FIG. 5). From this result, it can be seen that even in the case of a different analyte to be measured, employment of the polypeptide of the present invention as an separation-improving substance makes it possible to carry out a desired measurement (analysis) by use of HPLC under definite analysis conditions.

Example 15

A process for separating and measuring AFP's different in sugar chain structure by use of the polypeptide of the present invention

[Liquid reagent 1]

Except for using anti-AFP monoclonal antibody WA-2 (hereinafter abbreviated as "AFP-WA-2"; available from Wako Pure Chemical Industries, Ltd.; different in epitope from AFP-WA-1 and AFP-A4-4) as an antibody and Ala-(Tyr(SO$_3$H))$_5$-βAla (SEQ ID NO:13) as a polypeptide, a combined product of AFP-WA-2-Fab' and Ala-(Tyr(SO$_3$H))$_5$-βAla (SEQ ID NO:13) was prepared with the same reagents by the same procedure as described in Example 9. As liquid reagent 1, there was prepared 50 mM MES buffer (pH 6.5) containing 139 nM of the combined product, 1 mg/ml of Lens culinaris lectin (hereinafter abbreviated as "LCA"; available from Wako Pure Chemical Industries, Ltd.), 1 mM of magnesium chloride and 1 mM of calcium chloride.

[Liquid reagent 2]

As liquid reagent 2, there was used 50 nM MES buffer (pH 7.5) containing 147 nM of the AFP-WA-1.Fab'-POD prepared in Example 12, 156 nM of the combined product of Ala-(Tyr(SO$_3$H))$_8$-βAla (SEQ ID NO:17) and AFP-A4-4.Fab' prepared in Example 9, and 0.2 (w/v)% of a poly (vinyl alcohol).

[Samples]

AFP derived from human hepatoma was fractionated into LCA-unbound AFP and LCA-bound AFP by use of a column packed with LCA immobilized packing material therein. Each of them was added to human serum containing no AFP, to a concentration of 100 ng/ml, whereby sample 1 (containing the LCA-unbound AFP) and sample 2 (containing the LCA-bound AFP) were prepared.

[HPLC Conditions]

| | |
|---|---|
| Column: | POROS-DEAE (4.6 mm ID × 10 mm). |
| Buffer solution A: | 50 mM TAPS buffer (pH 8.5, containing 0.25 M NaCl). |
| Buffer solution B: | 50 mM TAPS buffer (pH 8.5, containing 3 M NaCl). |
| Substrate solution: | 50 mM MOPS buffer (pH 7.5, containing 90 mM 4-N-(4-carbobutyryl)aminophenol and 20 mM $H_2O_2$). |
| Gradient: | buffer solutions A + B, flow rate; 2 ml/min. |
| | 0 → 2 min.   B = 0% |
| | 2 → 4.5 min.   B = 13% |
| | 4.5 → 8 min.   B = 100% |
| | 8 → 8.5 min.   B = 0% |
| Post-column: | addition of POD substrate (a substrate solution, 0.1 ml/min). reaction at 60° C. for 30 sec. |
| Detection: | Fluorescence was measured at an excitation wavelength of 328 nm and an emission wavelength of 432 nm. |

[Measuring Procedure]

With 100 μl of liquid reagent 1 was mixed 10 μl of sample 1 or sample 2, and the reaction was carried out at 8° C. for 10 minutes. Then, 10 μl of liquid reagent 2 was added to the reaction solution and the resulting mixture was subjected to reaction for another 20 minutes. By HPLC under the above conditions, 80 μl of the reaction mixture was subjected to measurement (analysis).

[Results]

Figure 6:
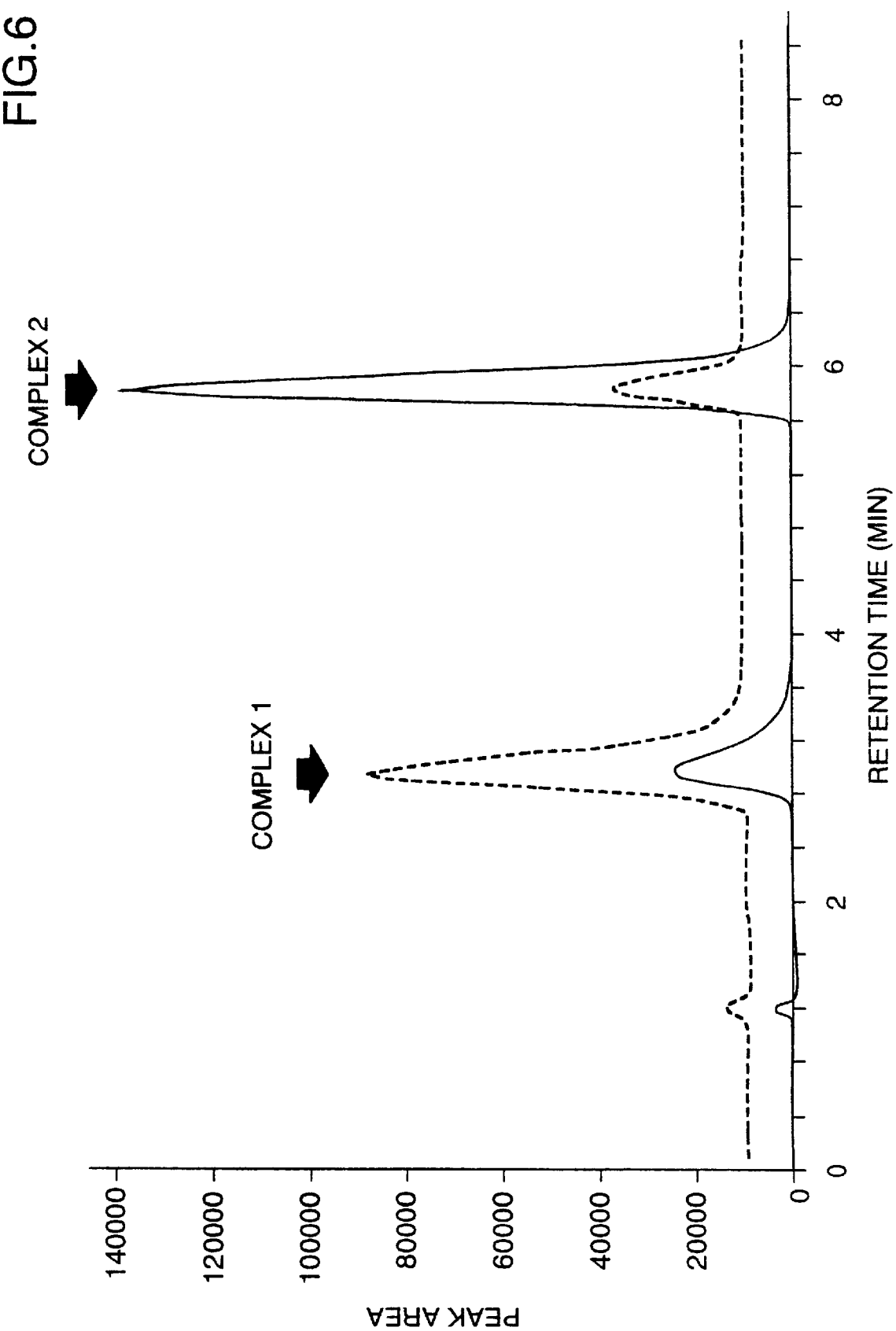
FIG. 6 shows elution patterns for analysis of samples by HPLC obtained in Example 15.

FIG. 6 shows the measurement results. In FIG. 6, the solid line (—) shows data obtained from sample 1, and the dotted line ( - - - ) data obtained from sample 2.

From the results shown in FIG. 6, the following can be seen: an antigen-antibody complex (complex 1) of AFP, the combined product of AFP-WA-2-Fab' and Ala-(Tyr(SO$_3$H))$_5$-βAla (SEQ ID NO:13), and AFP-WA-lFab'-POD was eluted at a position of 2.9 min; an antigen-antibody complex (complex 2) formed by introduction of the combined product of Ala-(Tyr(SO$_3$H))$_8$-βAla (SEQ ID NO:17) and AFP-A4-4.Fab' into complex 1 was eluted at a position of 5.8 min; and these complexes are certainly separated from each other.

From the results shown in FIG. 6, the following can also be seen: in the case of sample 1 containing LCA-unbound AFP, complex 2 formed by the attachment of the combined product of Ala-(Tyr(SO$_3$H))$_8$-βAla (SEQ ID NO:17) and AFP-A4-4.Fab' is mainly formed as antigen-antibody complex; and in the case of sample 2 containing LCA-attachable AFP, complex 1 is mainly formed as antigen-antibody complex. These results indicate that the combined product of Ala-(Tyr(SO$_3$H))$_8$-βAla (SEQ ID NO:17) and AFP-A4-4.Fab' is inhibited from reacting with AFP, by its competition with LCA.

The percentage of the amount of complex 1 formed, based on the total amounts of the two complexes formed (complex 1 percentage) was calculated (see Table 2) to find that this percentage reflects the proportin of LCA-bound AFP in each sample, namely, the proportin of LCA-bound AFP in each sample can be measured by utilizing said percentage.

Comparative Example

The same experiment as in Example 15 was carried out except for using a combined product of AFP-WA-2-Fab' and an aspartic acid polymer with an average molecular weight of 6,000 in place of the combined product of AFP-WA-2-Fab' and Ala-(Tyr(SO₃H))₅-βAla (SEQ ID NO:13), and using a combined product of AFP-A4-4.Fab' and an aspartic acid polymer with an average molecular weight of 28,800 in place of the combined product of Ala-(Tyr(SO₃H))₈-βAla (SEQ ID NO:17) and AFP-A4-4.Fab'. Then, the complex 1 percentage was calculated.

In addition, the same experiment as described above was carried out except that in place of the liquid reagent 1 used above, there was used a liquid reagent prepared by adding a γ-poly(glutamic acid) with an average molecular weight of 550,000 to the liquid reagent 1 to a concentration of 100 μg/ml.

The results obtained are also shown in Table 2.

TABLE 2

|  | Complex 1 percentage | |
| --- | --- | --- |
|  | Sample 1 | Sample 2 |
| Example 15 | 42.3% | 86.9% |
| Comparative Example | 58.4% | 82.9% |
| Comparative Example (in the presence of γPGA*) | 41.0% | 82.3% |

*γPGA: a γ-poly(glutamic acid) having an average molecular weight of 550,000.

From the results shown in Table 2, the following can be seen: when the process of Comparative Example (the process using the poly(aspartic acid)) is employed, the complex 1 percentage tends to become rather high in the case of sample 1, namely, a non-competitive reaction tends to take place, and an anionic additive such as γPGA should be added for repressing this phenomenon.

By contrast, when the polypeptide of the present invention is used, such an additive is not necessary. Therefore, the measuring process using the polypeptide of the present invention as a separation-improving substance is superior also in that respect to a measuring process using a polymer having carboxyl groups (e.g. poly(aspartic acid)) which has been used as separation-improving substance.

Although not apparent, the reason for the above-mentioned phenomenon is guessed as follows.

Since an anionic polymer such as poly(aspartic acid) has relatively large molecules, so that the antigen-antibody reaction is inhibited by electric charges, steric hindrance, etc., resulting in causing the above-mentioned phenomenon. On the other hand, it can be speculated that the polypeptide of the present invention has small molecules and hence hardly affects the antigen-antibody reaction.

Example 16

Investigation on the effect of addition of a surfactant to an eluent

[Reagent]

As a reagent, there was used 50 mM MOPS buffer (pH 7.5) containing 200 nM of the combined product of polypeptide 18 and AFP-A4-4.Fab' prepared in Example 9 and 100 nM of the AFP-WA-1.Fab'-POD.

[Sample]

The same as in Example 14.

[HPLC Conditions]

Column; POROS-DEAE (4.6 mm ID×10 mm).

| Buffer solution A: | 50 mM MOPS buffer (pH 7.5, containing 0.1 (w/v) % of a predetermined surfactant). |
| --- | --- |
| Buffer solution B: | 50 mM MOPS buffer (pH 7.5, containing 3 M NaCl and 0.1 (w/v) % of the predetermined surfactant). |
| Substrate solution: | 50 mM MOPS buffer (pH 7.5, containing 90 mM 4-N-(4-carbobutyryl)aminophenol and 20 mM H₂O₂). |
| Gradient: | buffer solutions A + B, flow rate; 1 ml/min. |
|  | 0 → 5 min.    A = 100% |
|  | 5 → 30 min.    B = 0 → 100% |
|  | 30 → 35 min.    B = 100% |
| Post-column: | addition of POD substrate (a substrate solution, 0.1 ml/min). reaction at 60° C. for 30 sec. |
| Detection: | Fluorescence was measured at an excitation wavelength of 328 nm and an emission wavelength of 432 nm. |

Table 3 shows surfactants used as the surfactant added to the eluents.

TABLE 3

| Surfactant | | |
| --- | --- | --- |
| No. | Name | Type |
| B | None | — |
| 1 | Polyoxyethylene higher alcohol | Nonionic |
| 2 | Polyoxyethylene (10) octylphenyl ether | Nonionic |
| 3 | n-Dodecyltrimethylammonium bromide | Cationic |
| 4 | Laurylbetaine | Amphoteric |
| 5 | Lauramide propylbetaine | Amphoteric |
| 6 | Coconut oil fatty acid amide propylbetaine | Amphoteric |
| 7 | 2-Undecyl-N-carboxymethyl-N-hydroxyethylimidazolium betaine | Amphoteric |
| 8 | N-eruroyl-N-methyl-β-alamine | Amphoteric |

[Measuring Procedure]

With 100 μl of the reagent was mixed 10 μl of the sample, and the reaction was carried out at 8° C. for 10 minutes. Then, 20 μl of the reaction mixture was subjected to measurement (analysis) by HPLC under the above conditions.

[Results]

Figure 7:
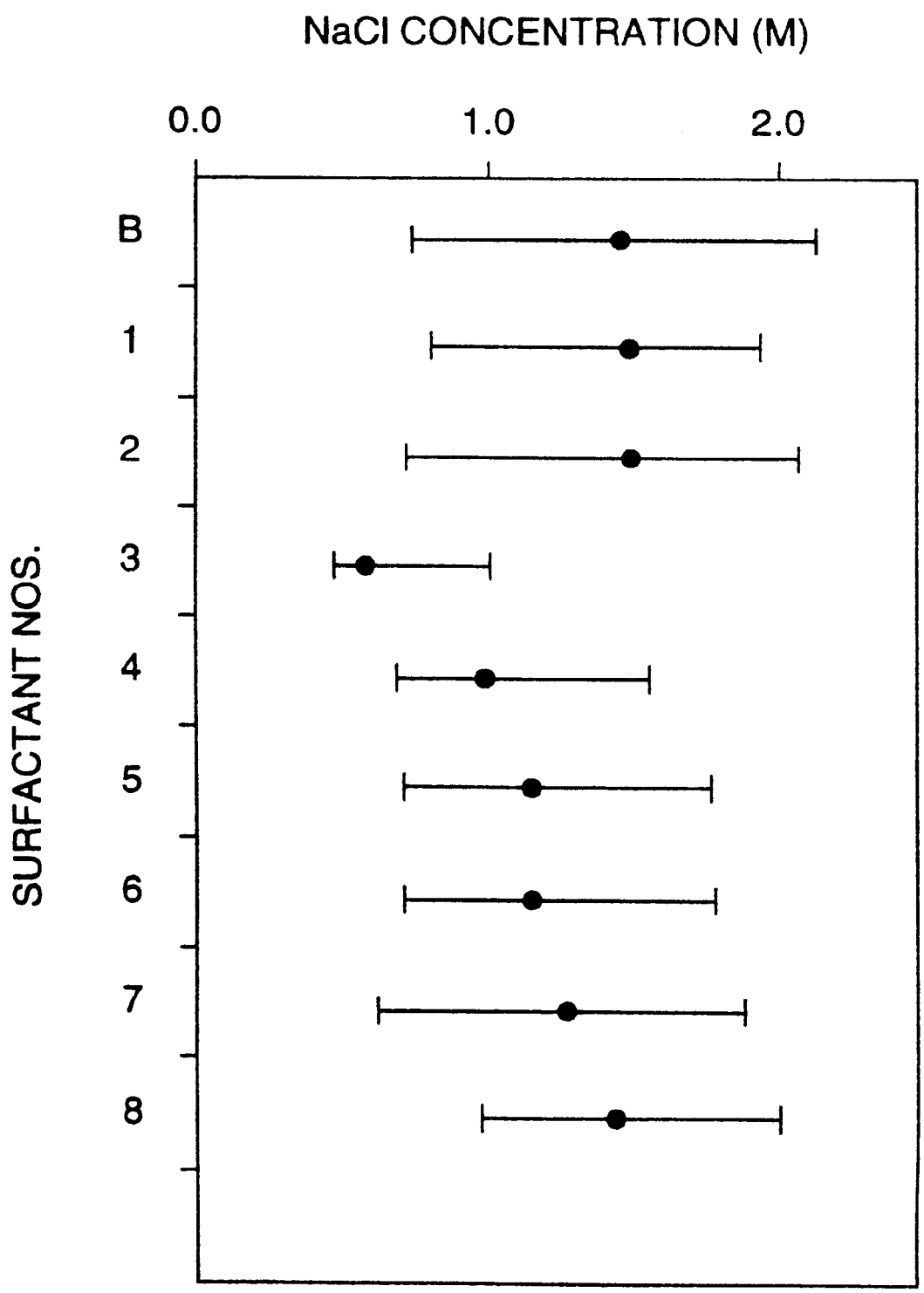
FIG. 7 shows elution positions of various antigen-antibody complexes by HPLC using an anion-exchange column obtained in Example 16.

FIG. 7 shows the eluting salt concentration and the peak width of an antigen-antibody complex of AFP which were determined by use of the eluent containing each of the various surfactants. In FIG. 7, ● shows a salt concentration at the top of elution peak, ┝━┥ shows a salt concentration range between the start and end of elution, i.e., a peak width. The Nos. on the axis of abscissa show the kind of the surfactants (the surfactant Nos. in Table 3).

The following can be seen from the results shown in FIG. 7.

(i) By adding the surfactant, the peak width can be narrowed, in other words, tailing of the peak during elution can be prevented, namely, the precision of measurement can be improved. This effect is remarkable in the case of the cationic surfactants and the amphoteric surfactants.

(ii) The eluting salt concentration (the elution position) is varied by the addition of the surfactant, namely, the eluting salt concentration of an objective antigen-antibody complex can be properly adjusted by choosing the surfactant properly.

Example 17

Separation by electrophoresis

[Samples]

Samples were prepared by diluting with 50 mM MOPS buffer solution (pH 7.5) the AFP-A4-4.Fab' produced in Example 10, a combined product of Ala-(Tyr(SO$_3$H))$_8$ (SEQ ID NO:18) and AFP-A4-4.Fab', the AFP-WA2.Fab' produced in Example 15, or a combined product of Ala-(Tyr(SO$_3$H))$_5$-βAla and AFP-WA2.Fab', respectively, so as to make the content 1 mg/ml.

[Measuring procedure]

Each sample in an amount of 4 μl was applied in the sample application wells on a side of 1% agarose-gel. The applied side was made a cathode, and electrolysis was conducted at a voltage of 200 V for 30 minutes, followed by dyeing of protein using Quick-CBB (a trade name, mfd. by Wako Pure Chemical Industries, Ltd.) to measure an Rf value of each sample.

[Results]

Rf values of the samples were as follows:

| Sample | Rf value |
| --- | --- |
| AFP-A4-F4 · Fab' | 0.38 |
| (SEQ ID NO: 18) [Ala-(Tyr(SO$_3$H))$_8$]-[AFP-A4 · 4Fab'] | 0.66 |
| AFP-WA2 · Fab' | 0.06 |
| (SEQ ID NO: 13) [Ala-(Tyr(SO$_3$H))$_5$-βAla]-[AFP-WA2 · Fab'] | 0.22 |

As shown above, by combining the sulfated peptide, the negative charge increases and the mobility is enlarged. Further, the larger the number of sulfuric acid residue in the sulfated peptide becomes, the larger the mobility becomes.

Example 18

Separation of reaction products of sulfated peptide-combined antibody and antigen

[Samples]

Samples were prepared by adding 50 μl of AFP solution adjusted with 50 mM MOPS buffer solution (pH 7.5) so as to make the content of AFP 0.5 mg/ml to 50 μl of a solution of the combined product of Ala-(Tyr(SO$_3$H))$_8$ (SEQ ID NO:18) and AFP-A4-4.Fab' obtained in Example 17 (1 mg/ml) in MOPS buffer solution (pH 7.5), 50 μl of a solution of the combined product of Ala-(Tyr(SO$_3$H))$_5$-βAla (SEQ ID NO:13) and AFP-WA2.Fab' obtained in Example 17 (1 mg/ml) in MOPS buffer solution (pH 7.5), or 50 μl of MOPS buffer solution (pH 7.5), followed by reaction at 37° C. for 30 minutes.

[Measuring Procedure]

Each sample in an amount of 4 μl was applied in the sample application wells on a side of 1% agarose-gel. The applied side was made a cathode, and electrolysis was conducted at a voltage of 200 V for 30 minutes, followed by antibody affinity metastasis (blotting) at room temperature for 30 minutes using an anti-AFP antibody-coated nitrocellulose membrane. This membrane was washed with a washing solution (0.9% NaCl) twice. After immersing this membrane in an anti-AFP antibody solution at 37° C. for 30 minutes, this membrane was washed twice using the washing solution. Then, this membrane was immersed in a POD labeled anti-IgG antibody solution at 37° C. for 30 minutes, followed by washing with the washing solution twice. Next, this membrane was color developed in a color developing solution (50 mM phosphate buffer solution (pH 7.5) containing 0.37 mM of Nitrotetrazolium blue, 2.6 mM of β-nicotinamide adenine dinucleotide, reduced form and 0.01% hydrogen peroxide), followed by measurement of Rf value of the antigen-antibody reaction product.

[Results]

Rf values of the samples were as follows:

| Sample | Rf value |
| --- | --- |
| Antigen-antibody reaction product of (SEQ ID NO: 18) [Ala-(Tyr(SO$_3$H))$_8$]-[AFP-A4-4 · Fab'] with AFP | 0.63 |
| Antigen-antibody reaction product of (SEQ ID NO: 13) [Ala-(Tyr(SO$_3$H))$_5$-βAla]-[AFP-WA2 · Fab'] with AFP | 0.20 |
| AFP | 0.85 |

As shown above, it is clear that Rf values of antigen-antibody reaction product of (SEQ ID NO:18) [Ala-(Tyr(SO$_3$H))8]-[AFP-A4-4.Fab'] with AFP and (SEQ ID NO:13) [Ala-(Tyr(SO$_3$H))$_8$-βAla]-[AFP-WA2.Fabl] with AFP are, respectively, almost the same as that of (SEQ ID NO:18) [Ala-(Tyr(SO$_3$H))$_8$]-[AFP-A4-4.Fab'] and [Ala-(Tyr(SO$_3$H))$_5$-βAla]-(AFP-WA2.Fab']. Thus, it is found that the negative charge of AFP dose not influence Rf values of antigen-antibody reaction product of [Ala-(Tyr(SO$_3$H))$_8$]-[AFP-A4-4.Fab'] with AFP and (SEQ ID NO:13) [Ala-(Tyr(SO$_3$H))$_5$-βAla]-[AFP-WA2.Fab'] with AFP.

As described above, the present invention provides a novel polypeptide and a process for measuring an analyte to be measured in a sample derived from a living body which uses the polypeptide. When a complex formed by the interaction between an analyte to be measured in a sample derived from a living body and an affinity substance is separated from free affinity substance and substances present in the sample which tend to affect the detection of the complex, by an anion-exchange method, said polypeptide can be used for separating the complex from the free affinity substance and the like more effectively. The present invention is markedly effective in that the measuring process of the present invention makes it possible to measure a trace component in a sample derived from a living body, such as serum, more easily in a much shorter time with higher precision as compared with, for example, conventional measuring processes according to EIA, RIA or the like, and processes using a polymer having carboxyl groups, as a separation-improving substance. Therefore, the present invention contributes greatly to the art.

What is claimed is:

1. A process for measuring an analyte comprising:
reacting a sample, of body fluids or cells, containing an analyte with a product which is a polypeptide bound to an affinity substance having an affinity for the analyte, said polypeptide having a total of 3 to 30 amino acid residues with at least three —$SO_3H$ or —$PO_3H_2$ groups introduced into the free reactive groups of the amino acid residues, whereby the reaction forms a resulting complex composed of the analyte and the product,
separating the resulting complex by subjecting the resulting complex to an anion exchange method,
eluting the separated resulting complex by increasing a concentration of a salt in an eluent, and
determining the amount of the analyte in the sample on the basis of the amount of the separated resulting complex eluted.

2. A process according to claim 1, wherein said polypeptide has four or more —$SO_3H$ or —$PO_3H_2$ groups.

3. A process according to claim 1, wherein said polypeptide has five or more —$SO_3H$ or —$PO_3H_2$ groups.

4. A process according to claim 1, wherein the anion-exchange method uses a material having anion-exchange capacity.

5. A process according to claim 1, wherein the anion-exchange method uses a HPLC apparatus equipped with a column packed with a packing material having anion-exchange capacity.

6. A process according to claim 1, wherein the anion-exchange method uses a material having anion-exchange capacity and a surfactant is added to the eluent used for the anion-exchange method.

7. A process according to claim 1, wherein the polypeptide is one member selected from the group consisting of Ala-(Ser($SO_3H$)$1_3$-βAla (SEQ ID NO:2), Ala-(Ser($SO_3H$))$_5$-βAla (SEQ ID NO:3), Ala-(Ser-($SO_3H$))$_8$-βAla (SEQ ID NO:4), (Ser($SO_3H$))$_8$-βAla (SEQ ID NO:5), Ala-Ala-Ala-(Ser($SO_3H$))$_{10}$ (SEQ ID NO:6), Ala-(Ser($SO_3H$))$_{20}$-βAla (SEQ ID NO:7), Ala-(Ser($SO_3H$)-Ser($SO_3H$)-Ser($SO_3H$)-βAla)$_3$ (SEQ ID NO:8), Ala-(Ser($SO_3H$)-Ser($SO_3H$)-βAla)$_5$ (SEQ ID NO:9), Ala-(Tyr($SO_3H$))$_3$-βAla (SEQ ID NO:10), Ala-(Tyr($SO_3H$))$_4$-βAla (SEQ ID NO:11), Ala-(Tyr($SO_3H$))$_4$ (SEQ ID NO:12), Ala-(Tyr-($SO_3H$))$_5$-βAla (SEQ ID NO:13), Ala-(Tyr($SO_3H$))$_5$(SEQ ID NO:14), Ala-(Tyr($SO_3H$))$_7$-βAla (SEQ ID NO:15), Ala-(Tyr($SO_3H$))$_7$ (SEQ ID NO:16), Ala-(Tyr($SO_3H$))$_8$-βAla (SEQ ID NO:17), Ala-(Tyr($SO_3H$))$_8$ (SEQ ID NO:18), Ala-(Tyr($SO_3H$))$_{10}$-

βAla (SEQ ID NO:19), Ala-(Ser(SO$_3$H))$_8$-(Tyr(SO$_3$H))$_5$ (SEQ ID NO:20), (Ser(SO$_3$H))$_8$-(Tyr(SO$_3$H)), (SEQ ID NO:21), Ala-(Tyr(PO$_3$H$_2$))$_5$-βAla (SEQ ID NO:22), and 4-maleimidobutytyl-Ala-(Tyr(PO$_3$H$_2$))$_5$-βAla (SEQ ID NO:22).

8. A process for measuring an analyte comprising:

reacting a sample of body fluids or cells containing an analyte with a reagent comprising a product which is a polypeptide bound to an affinity substance having a SH group and an affinity for the analyte, wherein the N-terminus of the polypeptide is bound through a spacer to a maleimido group, and said polypeptide has a total of 3 to 30 amino acid residues with at least three —SO$_3$H or —PO$_3$H$_2$ groups introduced into the free reactive groups of the amino acid residues, whereby the reaction forms a resulting complex composed of the analyte and the product, separating the resulting complex by subjecting the resulting complex to an anion exchange method, eluting the separated resulting complex by increasing a concentration of a salt in an eluent, and determining the amount of the analyte in the sample on the basis of the amount of the separated resulting complex eluted.

9. A process according to claim 8, wherein said polypeptide has four or more —SO$_3$H or —PO$_3$H$_2$ groups.

10. A process according to claim 8, wherein said polypeptide has five or more —SO$_3$H or —PO$_3$H$_2$ groups.

11. A process according to claim 8, wherein the anion-exchange method uses a material having anion-exchange capacity.

12. A process according to claim 8, wherein the anion-exchange method uses a HPLC apparatus equipped with a column packed with a packing material having anion-exchange capacity.

13. A process according to claim 8, wherein the anion-exchange method uses a material having anion-exchange capacity and a surfactant is added to the eluent used for the anion-exchange method.

14. A process according to claim 8, wherein the polypeptide is one member selected from the group consisting of Ala-(Ser(SO$_3$H))$_3$-βAla (SEQ ID NO:2), Ala-(Ser(SO$_3$H))$_5$-βAla (SEQ ID NO:3), Ala-(Ser-(SO$_3$H))$_8$-βAla (SEQ ID NO:4), (Ser(SO$_3$H))$_8$-βAla (SEQ ID NO:5), Ala-Ala-Ala-(Ser(SO$_3$H))$_{10}$ (SEQ ID NO:6), Ala-(Ser(SO$_3$H))$_{20}$-βAla (SEQ ID NO:7), Ala-(Ser(SO$_3$H)-Ser(SO$_3$H)-Ser(SO$_3$H)-βAla)$_3$ (SEQ ID NO:8), Ala-(Ser(SO$_3$H)-Ser(SO$_3$H)-βAla)$_5$ (SEQ ID NO:9), Ala-(Tyr(SO$_3$H))$_3$-βAla (SEQ ID NO:10), Ala-(Tyr(SO$_3$H))$_4$-βAla (SEQ ID NO:11), Ala-(Tyr(SO$_3$H))$_4$ (SEQ ID NO:12), Ala-(Tyr-(SO$_3$H))$_5$-βAla (SEQ ID NO:13), Ala-(Tyr(SO$_3$H))$_5$ (SEQ ID NO: 14), Ala-(Tyr(SO$_3$H))$_7$-βAla (SEQ ID NO: 15), Ala-(Tyr(SO$_3$H))$_7$ (SEQ ID NO: 16), Ala-(Tyr(SO$_3$H))$_8$-βAla (SEQ ID NO 17), Ala-(Tyr(SO$_3$H))$_8$ (SEQ ID NO: 18), Ala-(Tyr(SO$_3$H))$_{10}$-βAla (SEQ ID NO 19), Ala-(Ser(SO$_3$H))$_8$-(Tyr(SO$_3$H))$_5$ (SEQ ID NO:20), (Ser(SO$_3$H))$_8$-(Tyr(SO$_3$H))$_5$ (SEQ ID NO:21), Ala-(Tyr(PO$_3$H$_2$))$_5$-βAla (SEQ ID NO:22), and 4-maleimidobutytyl-Ala-(Tyr(PO$_3$H$_2$))$_5$-βAla (SEQ ID NO:22).

15. A process for measuring an analyte, comprising:

reacting a sample of body fluids or cells, containing an analyte with a product which is a polypeptide bound to an affinity substance having an affinity for the analyte, said polypeptide having a total of 3 to 30 amino acid residues with at least three —SO$_3$H or —PO$_3$H$_2$ groups introduced into the free reactive groups of the amino acid residues, whereby the reaction forms a resulting complex composed of the analyte and the product, separating the resulting complex by subjecting the resulting complex to a method for electrical separation of substances on the basis of their difference in electrical charge, determining the amount of the analyte in the sample on the basis of the amount of the separated resulting complex.

16. A process according to claim 15, wherein the separation of the resulting complex is conducted by electrophoresis.

17. A process according to claim 15, wherein said polypeptide has four or more —SO$_3$H or —PO$_3$H$_2$ groups.

18. A process according to claim 15, wherein said polypeptide has five or more —SO$_3$H or —PO$_3$H$_2$ groups.

19. A process according to claim 15, wherein the polypeptide is one member selected from the group consisting of Ala-(Ser(SO$_3$H))$_3$-βAla (SEQ ID NO:2), Ala-(Ser(SO$_3$H))$_5$-βAla (SEQ ID NO:3), Ala-(Ser-(SO$_3$H))$_8$-βAla (SEQ ID NO:4), (Ser(SO$_3$H))$_8$-βAla (SEQ ID NO:5), Ala-Ala-Ala-(Ser(SO$_3$H))$_{10}$(SEQ ID NO:6), Ala-(Ser(SO$_3$H))$_{20}$-βAla (SEQ ID NO:7), Ala-(Ser(SO$_3$H)-Ser(SO$_3$H)-Ser(SO$_3$H)-βAla)$_3$ (SEQ ID NO:8), Ala-(Ser(SO$_3$H)-Ser(SO$_3$H)-βAla)$_5$ (SEQ ID NO:9), Ala-(Tyr(SO$_3$H))$_3$-βAla (SEQ ID NO: 10), Ala-(Tyr(SO$_3$H))$_4$-βAla (SEQ ID NO:11), Ala-(Tyr(SO$_3$H))$_4$ (SEQ ID NO:12), Ala-(Tyr-(SO$_3$H))$_5$-βAla (SEQ ID NO: 13), Ala-(Tyr(SO$_3$H))$_5$ (SEQ ID NO: 14), Ala-(Tyr(SO$_3$H))$_7$-βAla (SEQ ID NO: 15), Ala-(Tyr(SO$_3$H))$_7$ (SEQ ID NO: 16), Ala-(Tyr(SO$_3$H))$_8$-βAla (SEQ ID NO: 17), Ala-(Tyr(SO$_3$H))$_8$ (SEQ ID NO: 18), Ala-(Tyr(SO$_3$H))$_{10}$-βAla (SEQ ID NO: 19), Ala-(Ser(SO$_3$H))$_8$-(Tyr(SO$_3$H))$_5$ (SEQ ID NO:20), (Ser(SO$_3$H))$_8$-(Tyr(SO$_3$H))$_5$ (SEQ ID NO:21), Ala-(Tyr(PO$_3$H$_2$))$_5$-βAla (SEQ ID NO:22), and 4-maleimidobutytyl-Ala-(Tyr(PO$_3$H$_2$))$_5$-βAla (SEQ ID NO:22).

* * * * *

UNITED STATES PATENT AND TRADEMARK OFFICE
CERTIFICATE OF CORRECTION

PATENT NO. : 6,300,079 B1
DATED : October 9, 2001
INVENTOR(S) : Imajo et al.

Page 1 of 1

It is certified that error appears in the above-identified patent and that said Letters Patent is hereby corrected as shown below:

<u>Column 62, claim 7,</u>
Line 55, change "Ala-(Ser($SO_3$H)1$_3$-βAla" to be -- Ala-(Ser($SO_3$H)$_3$-βAla --

Signed and Sealed this

Ninth Day of April, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.  : 6,300,079 B1
DATED       : October 9, 2001
INVENTOR(S) : Imajo et al.

It is certified that error appears in the above-identified patent and that said Letters Patent is hereby corrected as shown below:

<u>Column 62,</u>
Line 55, change "Ala-(Ser(SO$_3$H)1$_3$-βAla" to be -- Ala-(Ser(SO$_3$H))$_3$-βAla --

This certificate supersedes the Certificate issued April 9$^{th}$, 2002.

Signed and Sealed this

Fourteenth Day of January, 2003

JAMES E. ROGAN
*Director of the United States Patent and Trademark Office*